(12) United States Patent
Porath et al.

(10) Patent No.: US 10,179,933 B2
(45) Date of Patent: Jan. 15, 2019

(54) HYBRID NANOPORES AND USES THEREOF FOR DETECTION OF ANALYTES

(71) Applicant: YISSUM RESEARCH DEVELOPMENT COMPANY OF THE HEBREW UNIVERSITY OF JERUSALEM LTD., Jerusalem (IL)

(72) Inventors: Danny Porath, Jerusalem (IL); Oded Shoseyov, Carmei Yosef (IL); Yuval Nevo, Rehovot (IL); Ke Liu, Chavannes-près-Renens (CH); Dvir Marom Rotem, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 523 days.

(21) Appl. No.: 14/760,145

(22) PCT Filed: Feb. 6, 2014

(86) PCT No.: PCT/IL2014/050132
§ 371 (c)(1),
(2) Date: Jul. 9, 2015

(87) PCT Pub. No.: WO2014/122654
PCT Pub. Date: Aug. 14, 2014

(65) Prior Publication Data
US 2015/0354001 A1   Dec. 10, 2015

Related U.S. Application Data

(60) Provisional application No. 61/762,164, filed on Feb. 7, 2013.

(51) Int. Cl.
*C12Q 1/6869*    (2018.01)
*G01N 27/447*    (2006.01)
*G01N 33/487*    (2006.01)

(52) U.S. Cl.
CPC ..... *C12Q 1/6869* (2013.01); *G01N 27/44704* (2013.01); *G01N 27/44756* (2013.01); *G01N 33/48721* (2013.01)

(58) Field of Classification Search
None
See application file for complete search history.

(56) References Cited

U.S. PATENT DOCUMENTS

| | | |
|---|---|---|
| 2010/0331194 A1 | 12/2010 | Turner et al. |
| 2011/0053284 A1 | 3/2011 | Meller et al. |
| 2013/0203050 A1 | 8/2013 | Huber et al. |

FOREIGN PATENT DOCUMENTS

| | | |
|---|---|---|
| WO | 02/070647 A2 | 9/2002 |
| WO | 2004/022697 A2 | 3/2004 |
| WO | 2007/007325 A2 | 1/2007 |
| WO | 2011/027342 A2 | 3/2011 |
| WO | 2011/130312 A1 | 10/2011 |
| WO | 2012/160565 A1 | 11/2012 |

OTHER PUBLICATIONS

McGeoch et al., "Biological-to-electronic interface with pores to ATP synthase subunit C in silicon nitride barrier", Med. Biol. Eng. Comput. 38: 113-119 (2000).*
Hall, Adam R. et al., "Hybrid pore formation by directed insertion of α-haemolysin into solid-state nanopores", Nature Nanotechnology, Letters, 2010, pp. 874-877.
Wendell, David et al., "Translocation of double stranded DNA through membrane adapted phi29 motor protein nanopore", Nat. Nanotechnology, 2009, vol. 4, No. 11, pp. 765-772.
Cherf, Gerald M. et al., "Automated Forward and Reverse Ratcheting of DNA in a Nanopore at Five Angstrom Precision", Nature Biotechnology, 2012, vol. 30, No. 4, pp. 344-348.
Manrao, Elizabeth A. et al., "Reading DNA at single-nucleotide resolution with a mutant MspA nanopore and phi29 DNA polymerase", Nature Biotechnology, 2013, vol. 30, No. 4, pp. 349-353.
Luan, Binquan et al., "Base-By-Base Ratcheting of Single Stranded DNA through a Solid-State Nanopore", Physical Review Letters, Jun. 11, 2010, vol. 104, 238103-1-238103-4.
He, Yuhui et al., "Controlling DNA Translocation through Gate Modulation of Nanopore Wall Surface Charges", ACS Nano, 2011, vol. 5, No. 7, pp. 5509-5518.
Khoutorsky, Arkady et al., "Formation of Hydrophilic Nanochannels in the Membrane of Living Cells by the Ringlike Stable Protein-SP1", Nano Letters, 2011, vol. 11, pp. 2901-2904.
Wang, Hai-Yan et al., "Single-molecule DNA detection using a novel SP1 protein nanopore", Chem. Commun., 2013, vol. 49, No. 17, pp. 1741-1743.
White Ryan J. et al., "Single Ion-Channel Recordings Using Glass Nanopore Membranes", JACS Articles, J. Am. Chem. Soc., 2007, vol. 129, pp. 11766-11755.
Kowalczyk, Stefan W. et al., "Biomimetic nanopores: learning from and about nature", Cell Press, Trends in Biotechnology, 2011, vol. 29, No. 12, pp. 607-614.
Mohammad, Mohammad M. et al., "Engineering a Rigid Protein Tunnel for Biomolecular Detection", J. Am. Chem. Soc., 2012, vol. 134, pp. 9521-9531.
Bayley, Hagan et al., "Stochastic sensors inspired by biology", Nature, Sep. 13, 2001, vol. 413, pp. 226-230.
Li, Jiali et al., "Solid-state Nanopore for Detecting Individual Biopolymers", Methods Mol. Biol. 2009, vol. 544, pp. 81-93.

(Continued)

*Primary Examiner* — Anand U Desai

(74) *Attorney, Agent, or Firm* — Vorys, Sater, Seymour and Pease LLP

(57) ABSTRACT

The invention relates to a hybrid structure including perforated solid substrate having at least one nanopore perforating therethrough, and devices and uses thereof.

12 Claims, 19 Drawing Sheets

Specification includes a Sequence Listing.

(56) References Cited

OTHER PUBLICATIONS

Venkatesan, Bala Murali et al., "Nanopore sensors for nucleic acid analysis", Nature Nanotechnology, Oct. 2011, vol. 6; pp. 615-624.
Haque, Farzin et al., "Solid-State and Biological Nanopore for Real-Time Sensing of Single Chemical and Sequencing of DNA", Nano Today, 2013, vol. 8, No. 1, pp. 56-74.
Sanchez-Quesada et al., "Cyclic Peptides as Molecular Adapters for a Pore-Forming Protein", Journal of the American Chemical Society, vol. 122, No. 48, pp. 11757-11766, (2000).

* cited by examiner

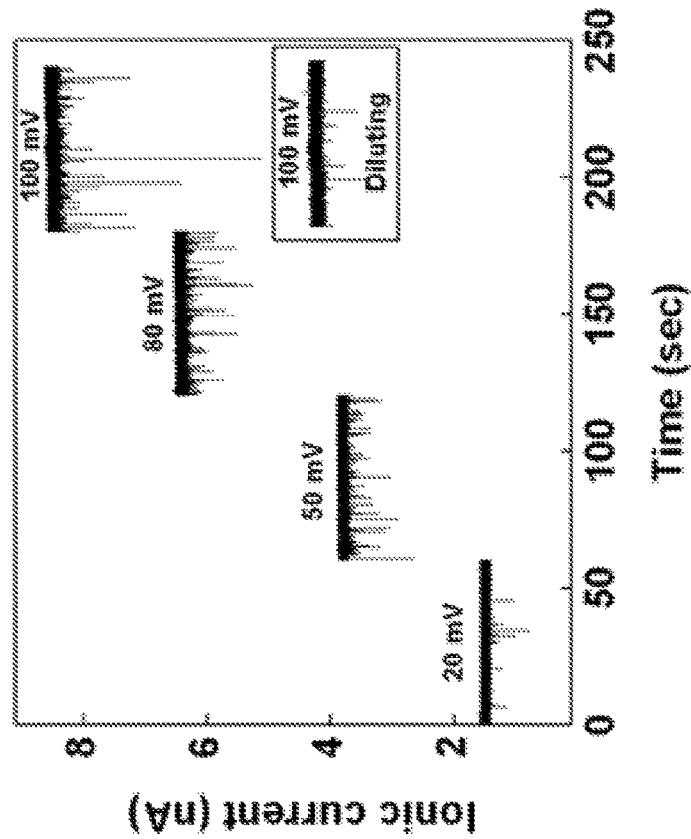
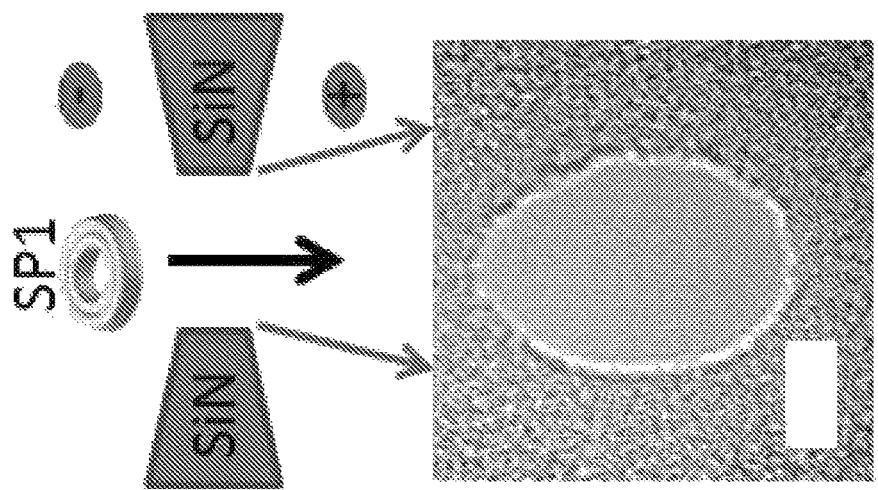
Figure 1B
Figure 1A

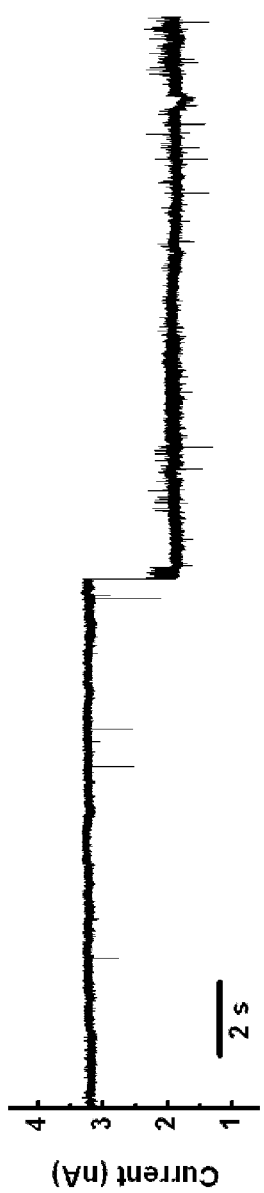
Figure 2C
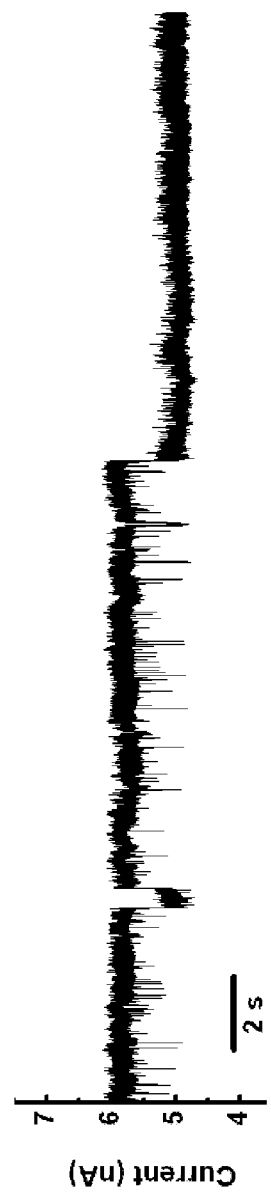
Figure 2D
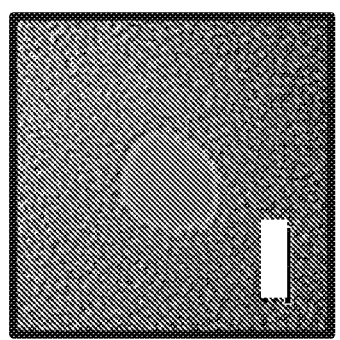
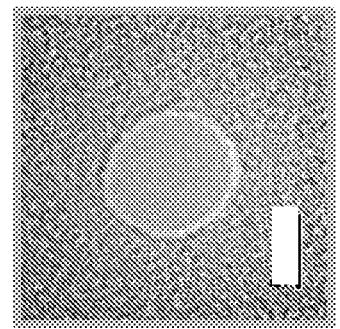

SEQUENCE LISTING

```
<160> NUMBER OF SEQ ID NOS: 18

<210> SEQ ID NO 1
<211> LENGTH: 108
<212> TYPE: PRT
<213> ORGANISM: Populus tremuloides

<400> SEQUENCE: 1

Met Ala Thr Arg Thr Pro Lys Leu Val Lys His Thr Leu Leu Thr Arg
1               5                   10                  15

Phe Lys Asp Glu Ile Thr Arg Glu Gln Ile Asp Asn Tyr Ile Asn Asp
            20                  25                  30

Tyr Thr Asn Leu Leu Asp Leu Ile Pro Ser Met Lys Ser Phe Asn Trp
        35                  40                  45

Gly Thr Asp Leu Gly Met Glu Ser Ala Glu Leu Asn Arg Gly Tyr Thr
    50                  55                  60

His Ala Phe Glu Ser Thr Phe Glu Ser Lys Ser Gly Leu Gln Glu Tyr
65                  70                  75                  80

Leu Asp Ser Ala Ala Leu Ala Ala Phe Ala Glu Gly Phe Leu Pro Thr
                85                  90                  95

Leu Ser Gln Arg Leu Val Ile Asp Tyr Phe Leu Tyr
            100                 105

<210> SEQ ID NO 2
<211> LENGTH: 114
<212> TYPE: PRT
<213> ORGANISM: Artificial Sequence
<220> FEATURE:
<223> OTHER INFORMATION: SP1 mutant variant

<400> SEQUENCE: 2

Met His His His His His His Ala Thr Arg Thr Pro Lys Leu Val Lys
1               5                   10                  15
```

```
His Thr Leu Leu Thr Arg Phe Lys Asp Glu Ile Thr Arg Glu Gln Ile
                20                  25                  30

Asp Asn Tyr Ile Asn Asp Tyr Thr Asn Leu Leu Asp Leu Ile Pro Ser
            35                  40                  45

Met Lys Ser Phe Asn Trp Gly Thr Asp Leu Gly Met Glu Ser Ala Glu
 50                      55                  60

Leu Asn Arg Gly Tyr Thr His Ala Phe Glu Ser Thr Phe Glu Ser Lys
 65                  70                  75                  80

Ser Gly Leu Gln Glu Tyr Leu Asp Ser Ala Ala Leu Ala Ala Phe Ala
                85                  90                  95

Glu Gly Phe Leu Pro Thr Leu Ser Gln Arg Leu Val Ile Asp Tyr Phe
            100                 105                 110

Leu Tyr

<210> SEQ ID NO 3
<211> LENGTH: 103
<212> TYPE: PRT
<213> ORGANISM: Artificial Sequence
<220> FEATURE:
<223> OTHER INFORMATION: SP1 mutant variant

<400> SEQUENCE: 3

Met Lys Leu Val Lys His Thr Leu Leu Thr Arg Phe Lys Asp Glu Ile
 1               5                  10                  15

Thr Arg Glu Gln Ile Asp Asn Tyr Ile Asn Asp Tyr Thr Asn Leu Leu
                20                  25                  30

Asp Leu Ile Pro Ser Met Lys Ser Phe Asn Trp Gly Thr Asp Leu Gly
            35                  40                  45

Met Glu Ser Ala Glu Leu Asn Arg Gly Tyr Thr His Ala Phe Glu Ser
 50                      55                  60

Thr Phe Glu Ser Lys Ser Gly Leu Gln Glu Tyr Leu Asp Ser Ala Ala
 65                  70                  75                  80

Leu Ala Ala Phe Ala Glu Gly Phe Leu Pro Thr Leu Ser Gln Arg Leu
                85                  90                  95

Val Ile Asp Tyr Phe Leu Tyr
            100

<210> SEQ ID NO 4
<211> LENGTH: 103
<212> TYPE: PRT
<213> ORGANISM: Artificial Sequence
<220> FEATURE:
<223> OTHER INFORMATION: SP1 mutant variant

<400> SEQUENCE: 4

Met Lys Leu Val Lys His Thr Leu Leu Thr Arg Phe Lys Asp Glu Ile
 1               5                  10                  15

Thr Arg Glu Gln Ile Asp Asn Tyr Ile Asn Asp Tyr Thr Asn Leu Leu
                20                  25                  30

Asp Leu Ile Pro Ser Cys Lys Ser Phe Asn Trp Gly Thr Asp Leu Gly
            35                  40                  45

Met Glu Ser Ala Glu Leu Asn Arg Gly Tyr Thr His Ala Phe Glu Ser
 50                      55                  60

Thr Phe Glu Ser Lys Ser Gly Leu Gln Glu Tyr Leu Asp Ser Ala Ala
 65                  70                  75                  80

Leu Ala Ala Phe Ala Glu Gly Phe Leu Pro Thr Leu Ser Gln Arg Leu
                85                  90                  95
```

Val Ile Asp Tyr Phe Leu Tyr
            100

<210> SEQ ID NO 5
<211> LENGTH: 103
<212> TYPE: PRT
<213> ORGANISM: Artificial Sequence
<220> FEATURE:
<223> OTHER INFORMATION: SP1 mutant variant

<400> SEQUENCE: 5

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
            20                  25                  30

Asp Leu Ile Pro Ser Met Lys Ser Phe Asn Trp Gly Thr Asp Leu Gly
        35                  40                  45

Met Glu Ser Ala Glu Leu Asn Arg Gly Tyr Thr His Ala Phe Glu Ser
    50                  55                  60

Thr Phe Glu Ser Lys Ser Gly Leu Gln Glu Tyr Cys Asp Ser Ala Ala
65                  70                  75                  80

Leu Ala Ala Phe Ala Glu Gly Phe Leu Pro Thr Leu Ser Gln Arg Leu
                85                  90                  95

Val Ile Asp Tyr Phe Leu Tyr
            100

<210> SEQ ID NO 6
<211> LENGTH: 102
<212> TYPE: PRT
<213> ORGANISM: Artificial Sequence
<220> FEATURE:
<223> OTHER INFORMATION: SP1 mutant variant

<400> SEQUENCE: 6

Lys Leu Val Lys His Thr Leu Leu Thr Arg Phe Lys Asp Glu Ile Thr
1               5                   10                  15

Arg Glu Gln Ile Asp Asn Tyr Ile Asn Asp Tyr Thr Asn Leu Leu Asp
            20                  25                  30

Leu Cys Pro Ser Met Lys Ser Phe Asn Trp Gly Thr Asp Leu Gly Met
        35                  40                  45

Glu Ser Ala Glu Leu Asn Arg Gly Tyr Thr His Ala Phe Glu Ser Thr
    50                  55                  60

Phe Glu Ser Lys Ser Gly Leu Gln Glu Tyr Leu Asp Ser Ala Ala Leu
65                  70                  75                  80

Ala Ala Phe Ala Glu Gly Phe Leu Pro Thr Leu Ser Gln Arg Leu Val
                85                  90                  95

Ile Asp Tyr Phe Leu Tyr
            100

<210> SEQ ID NO 7
<211> LENGTH: 103
<212> TYPE: PRT
<213> ORGANISM: Artificial Sequence
<220> FEATURE:
<223> OTHER INFORMATION: SP1 mutant variant

<400> SEQUENCE: 7

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu 20                  25                  30

Asp Leu Ile Pro Ser Met Lys Ser Phe Asn Trp Gly Thr Asp Leu Gly
            35                  40                  45

Met Glu Ser Ala Glu Leu Asn Arg Gly Tyr Thr His Ala Phe Glu Ser
    50                  55                  60

Thr Phe Glu Cys Lys Ser Gly Leu Gln Glu Tyr Leu Asp Ser Ala Ala
65                  70                  75                  80

Leu Ala Ala Phe Ala Glu Gly Phe Leu Pro Thr Leu Ser Gln Arg Leu
                85                  90                  95

Val Ile Asp Tyr Phe Leu Tyr
            100

<210> SEQ ID NO 8
<211> LENGTH: 327
<212> TYPE: DNA
<213> ORGANISM: Populus tremuloides

<400> SEQUENCE: 8
atggcaacca gaactccaaa gcttgtgaag cacacattgt tgactcggtt caaggatgag      60
atcacacgag aacagatcga caactacatt aatgactata ccaatctgct cgatctcatt     120
ccaagcatga agagtttcaa ttggggcacg gatctgggca tggagtctgc ggagctaaac     180
cgaggataca ctcatgcctt tgaatctaca tttgagagca gtctggtttt gcaagagtac     240
ctcgattctg ctgctcttgc tgcatttgca gaagggtttt tgcctacttt gtcacagcgt     300
cttgtgatag actactttct ctactaa                                         327

<210> SEQ ID NO 9
<211> LENGTH: 345
<212> TYPE: DNA
<213> ORGANISM: Artificial Sequence
<220> FEATURE:
<223> OTHER INFORMATION: SP1 mutant variant

<400> SEQUENCE: 9
atgcaccacc accaccacca cgcaaccaga actccaaaac ttgtgaagca cacattgttg      60
actcggttca aggatgagat cacacgagaa cagatcgaca actacattaa tgactatacc     120
aatctgctcg atctcattcc aagcatgaag agtttcaatt ggggcacgga tctgggcatg     180
gagtctgcgg agctaaaccg aggatacact catgcctttg aatctacatt tgagagcaag     240 tctggttttgc aagagtacct cgattctgct gctcttgctg catttgcaga agggttttg     300 cctactttgt cacagcgtct tgtgatagac tattttctct actaa                     345

<210> SEQ ID NO 10
<211> LENGTH: 312
<212> TYPE: DNA
<213> ORGANISM: Artificial Sequence
<220> FEATURE:
<223> OTHER INFORMATION: SP1 mutant variant

<400> SEQUENCE: 10
atgaagcttg tgaagcacac attgttgact cggttcaagg atgagatcac acgagaacag      60
atcgacaact acattaatga ctataccaat ctgctcgatc tcattccaag catgaagagt     120
ttcaattggg gcacggatct gggcatggag tctgcggagc taaaccgagg atacactcat     180
gcctttgaat ctacatttga gagcaagtct ggtttgcaag agtacctcga ttctgctgct     240
cttgctgcat ttgcagaagg gttttgcct acttttgtcac agcgtcttgt gatagactat     300

```
tttctctact aa                                                    312

<210> SEQ ID NO 11
<211> LENGTH: 312
<212> TYPE: DNA
<213> ORGANISM: Artificial Sequence
<220> FEATURE:
<223> OTHER INFORMATION: SP1 mutant variant

<400> SEQUENCE: 11
atgaagcttg tgaagcacac attgttgact cggttcaagg atgagatcac acgagaacag    60
atcgacaact acattaatga ctataccaat ctgctcgatc tcattccaag ctgcaagagt   120
ttcaattggg gcacggatct gggcatggag tctgcggagc taaaccgagg atacactcat   180
gcctttgaat ctacatttga gagcaagtct ggtttgcaag agtacctcga ttctgctgct   240
cttgctgcat ttgcagaagg ttttttgcct actttgtcac agcgtcttgt gatagactat   300
tttctctact aa                                                    312

<210> SEQ ID NO 12
<211> LENGTH: 312
<212> TYPE: DNA
<213> ORGANISM: Artificial Sequence
<220> FEATURE:
<223> OTHER INFORMATION: SP1 mutant variant

<400> SEQUENCE: 12
atgaagcttg tgaagcacac attgttgact cggttcaagg atgagatcac acgagaacag    60
atcgacaact acattaatga ctataccaat ctgctcgatc tcattccaag catgaagagt   120
ttcaattggg gcacggatct gggcatggag tctgcggagc taaaccgagg atacactcat   180
gcctttgaat ctacatttga gagcaagtct ggtttgcaag agtactgcga ttctgctgct   240
cttgctgcat ttgcagaagg ttttttgcct actttgtcac agcgtcttgt gatagactat   300
tttctctact aa                                                    312

<210> SEQ ID NO 13
<211> LENGTH: 312
<212> TYPE: DNA
<213> ORGANISM: Artificial Sequence
<220> FEATURE:
<223> OTHER INFORMATION: SP1 mutant variant

<400> SEQUENCE: 13
atgaagcttg tgaagcacac attgttgact cggttcaagg atgagatcac acgagaacag    60
atcgacaact acattaatga ctataccaat ctgctcgatc tctgcccaag catgaagagt   120
ttcaattggg gcacggatct gggcatggag tctgcggagc taaaccgagg atacactcat   180
gcctttgaat ctacatttga gagcaagtct ggtttgcaag agtacctcga ttctgctgct   240
cttgctgcat ttgcagaagg ttttttgcct actttgtcac agcgtcttgt gatagactat   300
tttctctact aa                                                    312

<210> SEQ ID NO 14
<211> LENGTH: 312
<212> TYPE: DNA
<213> ORGANISM: Artificial Sequence
<220> FEATURE:
<223> OTHER INFORMATION: SP1 mutant variant

<400> SEQUENCE: 14
atgaagcttg tgaagcacac attgttgact cggttcaagg atgagatcac acgagaacag    60
```

```
atcgacaact acattaatga ctataccaat ctgctcgatc tcattccaag catgaagagt    120
ttcaattggg gcacggatct gggcatggag tctgcggagc taaaccgagg atacactcat    180
gcctttgaat ctacatttga gtgcaagtct ggtttgcaag agtacctcga ttctgctgct    240
cttgctgcat ttgcagaagg gttttgcct actttgtcac agcgtcttgt gatagactat    300
tttctctact aa                                                       312
```

<210> SEQ ID NO 15
<211> LENGTH: 114
<212> TYPE: PRT
<213> ORGANISM: Artificial Sequence
<220> FEATURE:
<223> OTHER INFORMATION: SP1 mutant variant

<400> SEQUENCE: 15

```
Met Arg Lys Leu Pro Asp Ala Ala Thr Arg Thr Pro Lys Leu Val Lys
1               5                   10                  15

His Thr Leu Leu Thr Arg Phe Lys Asp Glu Ile Thr Arg Glu Gln Ile
                20                  25                  30

Asp Asn Tyr Ile Asn Asp Tyr Thr Asn Leu Leu Asp Leu Ile Pro Ser
            35                  40                  45

Met Lys Ser Phe Asn Trp Gly Thr Asp Leu Gly Met Glu Ser Ala Glu
        50                  55                  60

Leu Asn Arg Gly Tyr Thr His Ala Phe Glu Ser Thr Phe Glu Ser Lys
65                  70                  75                  80

Ser Gly Leu Gln Glu Tyr Leu Asp Ser Ala Ala Leu Ala Ala Phe Ala
                85                  90                  95

Glu Gly Phe Leu Pro Thr Leu Ser Gln Arg Leu Val Ile Asp Tyr Phe
            100                 105                 110

Leu Tyr
```

<210> SEQ ID NO 16
<211> LENGTH: 353
<212> TYPE: DNA
<213> ORGANISM: Artificial Sequence
<220> FEATURE:
<223> OTHER INFORMATION: SP1 mutant variant

<400> SEQUENCE: 16

```
atgcgcaaac ttccggatgc ggcaaccaga actccaaagc ttgtgaagca cacattgttg     60
actcggttca aggatgagat cacacgagaa cagatcgaca actacattaa tgactatacc    120
aatctgctcg atctcattcc aagcatgaag agtttcaatt ggggcacgga tctgggcatg    180
gagtctgcgg agctaaaccg aggatacact catgcctttg aatctacatt tgagagcaag    240
tctggtttgc aagagtacct cgattctgct gctcttgctg catttgcaga agggttttg    300 cctactttgt cacagcgtct tgtgatagac tactttctct actaaacgct cag           353
```

<210> SEQ ID NO 17
<211> LENGTH: 114
<212> TYPE: PRT
<213> ORGANISM: Artificial Sequence
<220> FEATURE:
<223> OTHER INFORMATION: SP1 mutant variant

<400> SEQUENCE: 17

```
Met Arg Lys Leu Pro Asp Ala Ala Thr Arg Thr Pro Lys Leu Val Lys
1               5                   10                  15
```

```
His Thr Leu Leu Thr Arg Phe Lys Asp Glu Ile Thr Arg Glu Gln Ile
            20              25              30

Asp Asn Tyr Ile Asn Asp Tyr Thr Asn Leu Leu Asp Leu Ile Pro Ser
        35              40              45

Cys Lys Ser Phe Asn Trp Gly Thr Asp Leu Gly Met Glu Ser Ala Glu
    50              55              60

Leu Asn Arg Gly Tyr Thr His Ala Phe Glu Ser Thr Phe Glu Ser Lys
65              70              75              80

Ser Gly Leu Gln Glu Tyr Leu Asp Ser Ala Ala Leu Ala Ala Phe Ala
            85              90              95

Glu Gly Phe Leu Pro Thr Leu Ser Gln Arg Leu Val Ile Asp Tyr Phe
            100             105             110

Leu Tyr

<210> SEQ ID NO 18
<211> LENGTH: 353
<212> TYPE: DNA
<213> ORGANISM: Artificial Sequence
<220> FEATURE:
<223> OTHER INFORMATION: SP1 mutant variant

<400> SEQUENCE: 18
atgcgcaaac ttccggatgc ggcaaccaga actccaaagc ttgtgaagca cacattgttg      60
actcggttca aggatgagat cacacgagaa cagatcgaca actacattaa tgactatacc     120
aatctgctcg atctcattcc aagctgtaag agtttcaatt ggggcacgga tctgggcatg     180
gagtctgcgg agctaaaccg aggatacact catgcctttg aatctacatt tgagagcaag     240
tctggtttgc aagagtacct cgattctgct gctcttgctg catttgcaga agggtttttg     300
cctactttgt cacagcgtct tgtgatagac tactttctct actaaacgct cag            353
```

HYBRID NANOPORES AND USES THEREOF FOR DETECTION OF ANALYTES

TECHNOLOGICAL FIELD

The present disclosure relates to structures and devices comprising hybrid nanopore structures and uses thereof.

BACKGROUND

Nanopore-based analysis has recently emerged as a promising tool enabling detection and analysis of analytes such as ions, nucleic acid molecules, polypeptides and others during their translocation through the nanopore. Nanopores are generally classified into three main groups: (i) synthetic nanopores (ii) biological nanopores and (iii) combination of biological and synthetic nanopores.

Hall A R et al [1] have inserted α-hemolysin into a solid-state nanopore by attaching a long DNA molecule to the protein. In addition, it was suggested to ratchet DNA through a nanopore in a controllable manner, e.g., phi29 molecular motor positioned on the entrance of the protein nanopore [2-4] and electrostatic screening by manipulating the charge distribution on the solid state nanopore wall [5-6].

WO11130312A1 [7] describes a nanopore device comprising a solid support and a cyclic molecule attached effectively by a covalent linkage to a zone on the interior sidewall surface of the channel.

Khoutorsky A et al [8] and WO2012/160565 [9 describe that SP1 and its derivatives can be used to generate hydrophilic nanochannels in the plasma membrane of living cells.

Wang et al 2013 [10] describe a system composed of SP1 nanopores in lipid bilayers for determination of short single stranded nucleic acid sequences.

REFERENCES

[1] A. R. Hall, A. Scott, D. Rotem, K. K. Mehta, H. Bayley and C. Dekker, *Nat. Nanotechnol.*, 2010, 5, 874-877.
[2] D. Wendell, P. Jing, J. Geng, V. Subramaniam, T J Lee, C. Montemagno and P. X. Guo, *Nat. Nanotechnol.*, 2009, 4, 765-772.
[3] G. M. Cherf, K. R. Lieberman, H. Rashid, C. E. Lam, K. Karplus and M. Akeson, *Nature Biotechnology*, 2012, 30, 344-348.
[4] E. A. Manrao, I. M. Derrington, A. H. Laszlo, K. W. Langford, M. K. Hopper, N. Gillgren, M. Pavlenok, M. Niederweis and J. H. Gundlach, *Nature Biotechnology*, 2012, 30, 349-U174.
[5] B. Q. Luan, H. B. Peng, S. Polonsky, S. Rossnagel, G. Stolovitzky and G. Martyna, *Phys. Rev. Lett.*, 2010, 104.
[6] Y. H. He, M. Tsutsui, C. Fan, M. Taniguchi and T. Kawai, *ACS Nano*, 2011, 5, 5509-5518.
[7] WO11130312
[8] A. Khoutorsky, A. Heyman, 0. Shoseyov, Me. Spica., *Nano Lett.* 2011, 11:2901-2904.
[9] WO2012/160565
[10] H. Y. Wang, Y. Li, L. X. Qin, A. Heyman, O. Shoseyov, I. Willner, Y T. Long, H. Tian, *Chem Commun* 2013, 49(17): 1741-1743.
[11] WO2002/070647
[12] WO2004/022697
[13] WO2007007325
[14] WO2011/027342

SUMMARY OF THE INVENTION

The present invention is based on the development of a unique platform which enables diagnosis and measurement of one or more of presence, identity and quantity of chemical or biological entities (analytes) in a sample. The unique platform of the invention is based on synthetic nanopores which are fabricated on a surface region of a device, which is tuned for measuring a parameter associated with the analytes passing through the nanopores.

In accordance with the invention, the nanopores are decorated, or incorporated with, or comprised of, or coated by ring-like polypeptides such as SP1 polypeptide and any fragment, peptide, analogues, homologous and derivatives thereof. The central pore (hole) of the ring-like polypeptide coincides and overlaps with the nanopore axis in such a way that a continuous channel is formed, connecting an opening face of the ring-like polypeptide and one opening of the nanopore. The continuous channel comprising both the polypeptide and the nanopore is hereby referred to as a hybrid nanopore.

The hybrid nanopores of the invention have been determined to exhibit different characteristics than the bare nanopore, free of the polypeptide. For example, as will be further demonstrated hereinbelow, it is shown that the translocation rate (time) of analytes through the hybrid nanopore was slower compared to the translocation rate through bare synthetic nanopores. The presence of the ring-like structure, e.g., SP1, in the hybrid nanopore not only affected the translocation rate (time), but also the conformation of the analyte during translocation. The hybrid nanopore was also found to selectively translocate a single conformation of the analyte.

Thus, control and fine-tuning of parameters such as translocation rate and analyte conformation through the nanopore permit a sensitive platform that enables a superior temporal resolution during the passing (translocation) of materials through the nanopore.

Therefore, in accordance with a first aspect, the present invention provides a hybrid structure comprising (a) a solid substrate having at least one nanopore perforating therethrough, and (b) at least one ring-like polypeptide situated at a region of said at least one nanopore, said region being selected from an opening of the nanopore and an interior region of said nanopore.

The binding of the at least one ring-like polypeptide to the nanopore is different than covalent binding. In some embodiments, the at least one nanopore comprises at its opening surface at least one ring-like polypeptide. In other embodiments, the at least one ring-like polypeptide is situated within the interior region of the nanopore.

According with the present disclosure, the solid substrate is the solid continuous material in which one or more nanopores are situated. The thickness of the substrate defines the length or depth of the nanopore structure. The solid substrate is characterized by having a first face or surface and an opposite face or a second face or surface. The distance between the first and second faces defines the thickness of the substrate and the length or depth of the nanopore structure.

In other words, when referring to the first face and second face of the substrate, it should be referred to the planar surfaces of the substrate that are the faces (top end and/or bottom) of the substrate. In some embodiments, the first surface or face and the second surface or face may be considered as parallel surfaces or substantially parallel surfaces.

Once the nanopores are perforated through the substrate, from one face to the other, the substrate may be referred to as a membrane.

When referring to the solid membrane, it should be noted that it does not encompass a cellular membrane or a bi-lipid layer membrane. In some embodiments, the solid substrate is synthetic. In some other embodiments, the solid substrate is an inorganic sheet. In some embodiments, the solid substrate comprises a material selected from silicon, aluminum, titanium, hafnium, graphene, glass, quartz, diamond and teflon.

In some embodiments, the solid substrate is comprised or is of a doped material, such as doped silicon or doped diamond or any of the materials listed above in doped forms.

In some other embodiments, the solid substrate is comprised or is of an undoped material, as listed above.

In some embodiments, the solid substrate is selected of a material comprising at least one of silicon nitride (SiN), silicon dioxide ($SiO_2$), aluminum oxide ($Al_2O_3$), titanium oxide ($TiO_2$) hafnium oxide ($HfO_2$) and graphene.

In some embodiments, the solid substrate consists or comprises silicon nitride.

The term "nanopore" as used herein denotes pores (holes, openings) present within the solid substrate, as defined. In the context of the present disclosure, the nanopores can be viewed as perforations having each a three dimensional representation of a channel (tunnel) with two openings at opposite sides of the solid substrate, wherein the two opening are connected by an interior defined by a height (length, depth). It should be noted that the nanopore in the context of the present disclosure is present within the solid substrate such that one of the nanopore openings is present at the first face of the substrate and the second opening is present at the second opposite face of the substrate.

The interior of the nanopore is spanned from one opening at the first surface (first opening) to an opening at the opposite surface (second opening) and connecting the two openings. The interior may be an open interior allowing flow throughout of any medium, e.g., a liquid medium or any material.

The first opening and the second opening of the nanopore are each characterized by a diameter that may be similar or different. When referring to opposite faces of the nanopore, it is noted that the two openings may be considered as essentially parallel openings or nearly parallel openings. In some embodiments, the two openings are co-axially positioned.

In some embodiments, each of the nanopores has, on average, a diameter of up to about 50 nm; in other embodiments, between about 1 nm to about 50 nm; in further embodiments, between about 1 nm to about 20 nm; in some further embodiments, between about 2 nm to about 10 nm; in some further embodiments, between about 3 nm to about 8 nm and in some other embodiments between 3 nm to 5 nm.

In some embodiments, the interior of the nanopore spanning the first opening and the second opening has a length from about 5 nm to about 50 nm; in some other embodiments, from about 10 nm to about 40 nm; in some further embodiments, from about 20 nm to about 35 nm.

The nanopores may be drilled in the solid substrate or alternatively may be manufactured by any available method known in the art. The fabrication of the nanopore(s) within the solid substrate may be achieved by any one or more of the following non-examples: feedback controlled low energy (0.5-5.0 keV) noble gas ion beam sculpting, high-energy (200-300 keV) electron beam illumination. The nanopore properties, such as for example diameter and length, may be determined by known methods in the field, such as transmission electron microscopy (TEM) and/or atomic force microscopy (AFM).

The solid substrate may comprise a plurality of nanopores. The plurality of nanopores may be arranged in an array of nanopores, wherein in the array the nanopores are arranged in groups or in a pattern, wherein each group or pattern of nanopores being homogeneous or heterogeneous in at least one parameter selected from nanopore density, nanopore size, nanopore depth and nanopore structure. For example, for certain applications, one group of nanopores may have on average the same pore diameter, while another group of nanopores is formed to have a different pore diameter. In other cases, each group of nanopores may be formed to comprise a plurality of nanopores having different pore diameter.

The hybrid structure described herein may be considered in accordance with some embodiments as a self assembled structure. The term self-assembly or any lingual variation thereof denoted a process in which the components of the hybrid nanopore structure are assembled into a structure (pattern) by a force which may or may not be imposed on the system to direct the assembly. In some embodiments, the process may be considered as being driven, without needing to introduce an external force. In some other embodiments, the process may use application of voltage. Thus, in line with some embodiments of the present invention, the hybrid structure may be considered as a self-assembled hybrid structure.

The ring-like polypeptide employed in accordance with the present invention is not limited to a specific protein and may be considered as suitable for any protein/polypeptide having a ring-like shape, namely an oligomeric polypeptide (protein) arranged in a circular ring shape (ring-like), having a central cavity (as inner hole) such that its center coincides with that of the nanopore. The ring-like polypeptide (protein) is further selected to form a stable interaction with the nanopore opening or the nanopore interior walls, and thus is selected not to associate with the nanopore region (opening or interior walls) covalently, either directly or via a linker having functional groups enabling the binding.

The ring-like polypeptide may be characterized by having an outer diameter defining an outer rim of the ring-like structure polypeptide and an inner diameter defining the diameter of the inner cavity (as inner hole). The plane comprising the inner diameter is referred herein as the X-Y plane and as such defines the planar orientation of the polypeptide. The ring-like polypeptide may be further characterized by having a height referred herein as a Z axis. The ring like polypeptide according to the present disclosure is characterized by having a symmetric structure when viewed along the X-Y plane. In some embodiments, the ring-like polypeptide is not characterized by having a mushroom like shape but rather a doughnut like shape.

In some embodiments, the at least one ring-like polypeptide has an inner diameter of between about 1 nm to about 10 nm. In some other embodiments, the at least one ring-like polypeptide has an inner diameter of between about 1 nm to about 7 nm. In some further embodiments, the at least one ring-like polypeptide has an inner diameter of between about 3 nm to about 4 nm.

In some embodiments, the at least one ring-like polypeptide has an outer diameter of between about 8 nm to about 18 nm. In some other embodiments, the at least one ring-like polypeptide has an outer diameter of between about 10 nm to about 15 nm. In some further embodiments, the at least one ring-like polypeptide has an outer diameter of between about 11 nm to about 13 nm.

The hybrid structure as described herein is characterized by having the inner diameter of the at least one ring-like polypeptide coincide with or match the nanopore diameter and as such, when viewed along the Z axis, the centers of the inner diameter of the polypeptide and the diameter of the nanopore are essentially at the same location.

The location of the at least one ring like polypeptide within the interior of the nanopore is dictated by a balance between the outer diameter of the ring like polypeptide and the diameter of the nanopore. The ring-like polypeptide may have an outer diameter (namely the diameter of the entire polypeptide referred to herein as outer rim) that is larger, equal or smaller than the diameter of the nanopore. In some embodiments, the diameter of at least one nanopore is smaller or equal to the outer diameter of the at least one ring-like polypeptide. In some embodiments, the outer diameter/rim of the polypeptide is larger than that of the nanopore and as such the polypeptide cannot enter the interior of the nanopore while adopting a conformation at which the diameters centers are co-axially oriented.

In some embodiments, the at least one ring-like polypeptide is situated on an opening of the nanopore. In connection with the present disclosure, the surface (face) associated with the polypeptide is a first surface of the membrane. This can be viewed as at least one ring-like polypeptide located on top of the first opening of the nanopore.

In some embodiments, the diameter of at least one nanopore is larger than the outer diameter of the at least one ring-like polypeptide. In some embodiments, the at least one ring-like polypeptide may be located within the nanopore interior surface.

The ring-like polypeptide may be selected to comprise several monomeric subunits, being either identical (homo) or different (hetero) from each other, together forming a ring-like structure, e.g., complex polypeptides. The polypeptide may be a native homo-oligomer or hetero-oligomer comprising monomeric subunits arranged, for example, in a concentric arrangement.

The ring-like polypeptide that may be used in accordance with the invention may be a heat shock protein (HSP). The expression of HSP is increased when cells are exposed to elevated temperatures and other stress. The ring-like polypeptide may be for example HSP 60, HSP 70, HSP90 or thermolysin.

In some embodiments, the ring-like polypeptide is stable protein 1 (SP1) polypeptide [11-13].

The preparation, structural modification (mutations) and characteristics of SP1 are disclosed in international patent application nos. WO2002/070647 [11], WO2004/022697 [12], WO2007/007325 [13] and WO2011/027342 [14], and corresponding US patent applications, each being incorporated herein by reference.

As used herein "SP1" (stable protein 1) represents a homo-dodecamer oligomeric protein having a ring-shape, referred also as a "doughnut-like" shape. SP1 polypeptide is naturally localized in the cytoplasm of plant cells and is not found in animal, e.g., mammalian (human or non-human) cells. SP1 has a net charge of −12 charge units that are distributed on its surface.

When referring to SP1 it may be considered as consisting of 12 monomers which may be identical and as such having a molecular weight of 149 kDa. It is an extremely stable ($T_M$~109° C.) and is considered as a boiling stable polypeptide, having a structural oligomeric stability following treatment at about 95° C., in an aqueous solution, for at least 10 minutes, as determined by a size fractionation assay. In addition, SP1 is characterized as a denaturant-stable polypeptide, having a structural oligomeric stability of an oligomeric protein following treatment in aqueous solution containing 1:2,000 molar ratio (monomer:SDS), as determined by a size fractionation assay. SP1 polypeptide was shown to be a functionally related protein that is involved in the folding and unfolding of other proteins.

In the context of the present disclosure, when referring to SP1 it should be considered to encompass SP1 and any fragment, peptide, variant, analogues, homologue and derivatives thereof. Further, in the context of the present disclosure, when referring to SP1 and any fragment, peptide, variant, analogues, homologue and derivatives thereof it should be considered to encompass also a hetero-dodecamer, namely a polypeptide having monomers with different sequences.

It should be noted that the different SEQ ID NOs provided herein define amino acid sequences of one monomer of SP1 or nucleotide sequences encoding one monomer of SP1.

In some embodiments, the SP1 is the wild type polypeptide (a monomer of which disclosed, for example, in [14] as SEQ ID NO: 4; being referred to herein as SEQ ID NO: 1) or any fragment, peptide, variant, analogues, homologue and derivatives thereof disclosed, for example, in any of references [11-14], each being incorporated herein by reference). In some embodiments, the SP1 polypeptide is the wild type polypeptide (a monomer of which is disclosed, for example, in [14] as SEQ ID NO: 4 being referred to herein as SEQ ID NO: 1) or any derivatives thereof (disclosed, for example, in any of references [11-14], each being incorporated herein by reference).

It should be appreciated that in certain embodiments, SP1 protein refers to the SP1 polypeptide as denoted by SEQ ID NO: 1. As noted throughout, this refers to a sequence of one monomer of the SP1. Specifically, the SP1 protein comprises an amino acid sequence of one monomer of 108 amino acid residues as denoted by GenBank Accession No. AJ276517.1.

In certain embodiments, the SP1 polypeptide comprises the amino acid sequence MATRTPKLVKHTLLTRFKDEITREQIDNYINDYTNLLDLIPSMKSFNWGTDLGA ELNRGYTHAFESTFESKSGLQEYLDSAALAAFAEG-FLPTLSQRLVIDYFLY as denoted by SEQ ID NO: 1.

In some embodiments, the SP1 polypeptide is a polypeptide encoded by the polynucleotide deposited in NCBI under GenBank: AJ276517.1 (SEQ ID NO:8).

In some embodiments, the SP1 polypeptide is wild-type SP1 polypeptide (SEQ ID NO:1).

As may be appreciated by those versed in the art, genetic modification of a polypeptide is of common practice and includes mutations in the polynucleotide encoding the respective polypeptide, such that a selective mutation in the nucleotide sequence would result in a desired amino acid mutation. Any mutation of the SP1 polypeptide referred to herein is a mutation based on the wild-type polypeptide. Mutations in the polypeptide may include substitutions (mutations) of at least one amino acid, deletion of at least one amino acid or addition of at least one amino acid. Thus, the polypeptide used in accordance with the present invention may be selected from the wild-type SP1 polypeptide, cysteine mutated/substituted/added SP1 polypeptide, histidine mutated/substituted/added SP1 polypeptide and methionine mutated/substituted/added SP1 polypeptide.

Certain embodiments of the invention involve SP1 polypeptide and any fragment, peptide, analogues, homologue and derivatives thereof. It should be appreciated that such peptides (polypeptides) or amino acid sequences are preferably isolated and purified molecules, as defined herein. The term "purified" or "isolated" refers to molecules, such as amino acid sequences, or peptides that are removed from their natural environment, isolated or separated. An "isolated peptide" is therefore a purified amino acid sequence. "Substantially purified" molecules are at least 60% free, preferably at least 75% free, and more preferably at least 90% free from other components with which they are naturally associated. As used herein, the term "purified" or "to purify" also refers to the removal of contaminants from a sample.

The term "polypeptide" as used herein refers to amino acid residues, connected by peptide bonds. A polypeptide sequence is generally reported from the N-terminal end containing free amino group to the C-terminal end containing free carboxyl group.

More specifically, "amino acid molecule", "amino acid sequence" or "peptide sequence" is the order in which amino acid residues connected by peptide bonds, lie in the chain in peptides and proteins. The sequence is generally reported from the N-terminal end containing free amino group to the C-terminal end containing amide. Amino acid sequence is often called peptide, protein sequence if it represents the primary structure of a protein, however one must discern between the terms "Amino acid sequence" or "peptide sequence" and "protein", since a protein is defined as an amino acid sequence folded into a specific three-dimensional configuration and that had typically undergone post-translational modifications, such as phosphorylation, acetylation, glycosylation, manosylation, amidation, carboxylation, sulfhydryl bond formation, cleavage and the like.

Amino acids, as used herein refer to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same fundamental chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid Amino acids may be referred to herein by either their commonly known three letter symbols or by the one-letter symbols recommended by the IUPAC-IUB Biochemical Nomenclature Commission.

It should be noted that in addition to any of the SP1 derived fragments or peptides encompassed herein, the invention further encompasses any derivatives, analogues, variants or homologues of any of the SP1 polypeptide. The term "derivative" is used to define amino acid sequences (polypeptide), with any insertions, deletions, substitutions and modifications to the amino acid sequences (polypeptide). In some embodiments, these do not alter the activity of the original polypeptides. By the term "derivative" it is also referred to homologues, variants and analogues thereof, as well as covalent modifications of a polypeptides made according to the present invention.

In some embodiments, the SP1 polypeptide comprises additional histidine residues (SEQ ID NO:2) and encoded by the polynucleotide having the sequence SEQ ID NO:9. More specifically, the SP1 polypeptide comprise the amino acid sequence MHHHHHHATRTPKLVKHTLLTRFKDEITREQIDNYINDYTNLLDLIPSMKSFNW GTDLGMESAELNRGYTHAFESTFESKSGLQEYLDSAALAAFAEGFLPTLSQRLV IDYFLY denoted as SEQ ID NO:2. As such, the 6His-SP1 derivative describes herein corresponds to SEQ ID NO:2.

In further embodiments, the SP1 polypeptide is a homologous variant to wild type SP1. The homologous variant may comprise for example deletion of amino acids in the N-terminal region of the wild type SP1.

In some embodiments, the SP1 polypeptide is a polypeptide with a deletion of amino acids in the N-terminal region. This variant SP1 polypeptide having SEQ ID NO:3, is encoded by the polynucleotide having the sequence SEQ ID NO:10.

In some embodiments, the SP1 polypeptide comprises mutations of amino acids to cysteine. Non-limiting examples of such polypeptides comprise: SEQ ID NO:4 (encoded by the polynucleotide having the sequence SEQ ID NO:11); SEQ ID NO:5 (encoded by the polynucleotide having the sequence SEQ ID NO:12); SEQ ID NO:6 (encoded by the polynucleotide having the sequence SEQ ID NO:13); and SEQ ID NO:7 (encoded by the polynucleotide having the sequence SEQ ID NO:14).

In some other embodiments, the SP1 polypeptide comprises the amino acid sequence denoted as SEQ ID NO:4. In some further embodiments, the SP1 polypeptide is a polypeptide encoded by the polynucleotide denoted by SEQ ID NO:11.

In some other embodiments, the SP1 polypeptide comprises the amino acid sequence denoted as SEQ ID NO:5. In some further embodiments, the SP1 polypeptide is a polypeptide encoded by the polynucleotide denoted by SEQ ID NO:12.

In some other embodiments, the SP1 polypeptide comprises the amino acid sequence denoted as SEQ ID NO:6. In some further embodiments, the SP1 polypeptide is a polypeptide encoded by the polynucleotide denoted by SEQ ID NO:13.

In some other embodiments, the SP1 polypeptide comprise the amino acid sequence denoted as SEQ ID NO:7. In some further embodiments, the SP1 polypeptide is a polypeptide encoded by the polynucleotide denoted by SEQ ID NO:14.

In some other embodiments, the SP1 polypeptide comprises the amino acid sequence denoted as SEQ ID NO:15. In some further embodiments, the SP1 polypeptide is a polypeptide encoded by the polynucleotide denoted by SEQ ID NO:16.

In some embodiments, the SP1 polypeptide comprises the amino acid sequence MRKLPDAATRTPKLVKHTLLTRFKDEITREQIDNYINDYTNLLDLIPSMKSFNW GTDLGMESAELNRGYTHAFESTFESKSGLQEYLDSAALAAFAEGFLPTLSQRLV IDYFLY denoted as SEQ ID NO:15.

In some other embodiments, the SP1 polypeptide comprises the amino acid sequence denoted as SEQ ID NO:17. In some further embodiments, the SP1 polypeptide is a polypeptide encoded by the polynucleotide denoted by SEQ ID NO:18.

In some embodiments, the SP1 polypeptide comprises the amino acid sequence MRKLPDAATRTPKLVKHTLLTRFKDEITREQIDNYINDYTNLLDLIPSCKSFNW GTDLGMESAELNRGYTHAFESTFESKSGLQEYLDSAALAAFAEGFLPTLSQRLV IDYFLY denoted as SEQ ID NO:17.

In the context of the present disclosure, any reference to any one SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 15 or SEQ ID NO: 17, is regarded as a reference to one monomer of the dodecamer SP1 polypeptide. In addition, when referring to sequences denoted by SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 16 or SEQ ID NO: 18 it should be regarded as referring a polynucleotide encoding one monomer of the dodecamer SP1 polypeptide.

The SP1 may be genetically manipulated to comprise 12 monomers in which at least one, at least two, at least three, at least four, at least five, at least six, at least seven, at least eight, at least nine, at least ten, at least eleven or at least twelve monomers are the same or different. In some embodiments, at least one, at least two, at least three, at least four, at least five, at least six, at least seven, at least eight, at least nine, at least ten, at least eleven or at least twelve of the monomers are independently selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 15 and SEQ ID NO: 17.

The polypeptides employed in accordance with the invention may be produced synthetically, or by recombinant DNA technology. Methods for producing polypeptides peptides are well known in the art.

In some embodiments, the SP1 derivatives include, but are not limited to, polypeptides that differ in one or more amino acids in their overall sequence from the polypeptides defined herein (either the SP1 protein or any fragment or peptide derived therefrom according to the invention), polypeptides that have deletions, substitutions, inversions or additions.

In some embodiments, the derivatives are polypeptides, which differ from the polypeptides specifically defined in the present invention by insertions of amino acid residues. It should be appreciated that by the terms "insertions" or "deletions it is meant any addition or deletion, respectively, of amino acid residues to the polypeptides, of between 1 to 50 amino acid residues, between 20 to 1 amino acid residues, and specifically, between 1 to 10 amino acid residues. Insertions or deletions may be of any one of 1, 2, 3, 4, 5, 6, 7, 8, 9, or 10 amino acids and may occur at any position of the modified peptide, as well as in any of the N' or C' termini thereof.

The peptides of the invention may all be positively charged, negatively charged or neutral. In addition, they may be in the form of a dimer, a multimer or in a constrained conformation, which can be attained by internal bridges, short-range cyclizations, extension or other chemical modifications.

The polypeptides of the invention can be coupled (conjugated) through any of their residues to another peptide or agent. For example, the polypeptides of the invention can be coupled through their N-terminus to a lauryl-cysteine (LC) residue and/or through their C-terminus to a cysteine (C) residue.

Further, the peptides may be extended at the N-terminus and/or C-terminus thereof with various identical or different amino acid residues. As an example for such extension, the peptide may be extended at the N-terminus and/or C-terminus thereof with identical or different amino acid residue/s, which may be naturally occurring or synthetic amino acid residue/s. An additional example for such an extension may be provided by peptides extended both at the N-terminus and/or C-terminus thereof with a cysteine residue. Naturally, such an extension may lead to a constrained conformation due to Cys-Cys cyclization resulting from the formation of a disulfide bond. Another example may be the incorporation of an N-terminal lysyl-palmitoyl tail, the lysine serving as linker and the palmitic acid as a hydrophobic anchor. In addition, the peptides may be extended by aromatic amino acid residue/s, which may be naturally occurring or synthetic amino acid residue/s, for example, a specific aromatic amino acid residue may be tryptophan. The peptides may be extended at the N-terminus and/or C-terminus thereof with various identical or different organic moieties, which are not naturally occurring or synthetic amino acids. As an example for such extension, the peptide may be extended at the N-terminus and/or C-terminus thereof with an N-acetyl group.

For every single peptide sequence defined herein, this invention includes the corresponding retro-inverse sequence wherein the direction of the peptide chain has been inverted and wherein all the amino acids belong to the D-series.

The invention also encompasses any homologues of the polypeptides (either the SP1 protein or any fragments or peptides thereof) specifically defined by their amino acid sequence according to the invention. The term "homologues" is used to define amino acid sequences (polypeptide) which maintain a minimal homology to the amino acid sequences defined by the invention, e.g. preferably have at least about 65%, more preferably at least about 75%, even more preferably at least about 85%, most preferably at least about 95% overall sequence homology with the amino acid sequence of any of the polypeptide as structurally defined above, e.g. of a specified sequence, more specifically, an amino acid sequence of the polypeptides as denoted by any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 15, SEQ ID NO: 17.

More specifically, "homology" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N-nor C-terminal extensions nor insertions or deletions shall be construed as reducing identity or homology. Methods and computer programs for the alignment are well known in the art.

In some embodiments, the present invention also encompasses polypeptides which are variants of, or analogues to, the polypeptides specifically defined in the invention by their amino acid sequence. With respect to amino acid sequences, one of skill will recognize that individual substitutions, deletions or additions to peptide, polypeptide, or protein sequence thereby altering, adding or deleting a single amino acid or a small percentage of amino acids in the encoded sequence is a "conservatively modified variant", where the alteration results in the substitution of an amino acid with a chemically similar amino acid.

Conservative substitution tables providing functionally similar amino acids are well known in the art. Such conservatively modified variants are in addition to and do not exclude polymorphic variants, interspecies homologues, and alleles and analogous peptides of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

More specifically, amino acid "substitutions" may be the result of replacing one amino acid with another amino acid having similar structural and/or chemical properties, i.e., conservative amino acid replacements Amino acid substitutions may be made on the basis of similarity in polarity, charge, solubility, hydrophobicity, hydrophilicity, and/or the amphiphathic nature of the residues involved. For example, nonpolar "hydrophobic" amino acids are selected from the group consisting of Valine (V), Isoleucine (I), Leucine (L), Methionine (M), Phenylalanine (F), Tryptophan (W), Cysteine (C), Alanine (A), Tyrosine (Y), Histidine (H), Threonine (T), Serine (S), Proline (P), Glycine (G), Arginine (R) and Lysine (K); "polar" amino acids are selected from the group consisting of Arginine (R), Lysine (K), Aspartic acid (D), Glutamic acid (E), Asparagine (N), Glutamine (Q); "positively charged" amino acids are selected form the group consisting of Arginine (R), Lysine (K) and Histidine (H) and wherein "acidic" amino acids are selected from the group consisting of Aspartic acid (D), Asparagine (N), Glutamic acid (E) and Glutamine (Q).

The derivatives of any of the polypeptides according to the present invention, e.g. of a specified sequence of any one of the polypeptides denoted by SEQ ID NO: 1, SEQ ID NO:2, SEQ ID NO:3, SEQ ID NO:4, SEQ ID NO:5, SEQ ID NO:6, SEQ ID NO:7, SEQ ID NO:15 or SEQ ID NO:17 may vary in their size and may comprise the full length polypeptide or any fragment thereof. In certain embodiments, the polypeptides may comprise one or more amino acid residue surrogate. An "amino acid residue surrogate" as herein defined is an amino acid residue or peptide employed to produce mimetics of critical function domains of peptides.

Examples of amino acid surrogate include, but are not limited to chemical modifications and derivatives of amino acids, stereoisomers and modifications of naturally occurring amino acids, non-protein amino acids, post-translationally modified amino acids, enzymatically modified amino acids, and the like. Examples also include dimers or multimers of peptides. An amino acid surrogate may also include any modification made in a side chain moiety of an amino acid. This thus includes the side chain moiety present in naturally occurring amino acids, side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like.

It should be appreciated that the invention further encompass any of the peptides, any serogates thereof, any salt, base, ester or amide thereof, any enantiomer, stereoisomer or disterioisomer thereof, or any combination or mixture thereof. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts.

It should be noted that the invention further encompasses any peptidomimetic compound mimicking the polypeptide of the invention, namely SP1 and any fragment or peptide thereof. When referring to peptidomimetics, what is meant is a compound that mimics the conformation and desirable features of a particular natural peptide but avoids the undesirable features, e.g., flexibility and bond breakdown. From chemical point of view, peptidomimetics can have a structure without any peptide bonds; nevertheless, the compound is peptidomimetic due to its chemical properties and not due to chemical structure. Peptidoinimetics (both peptide and non-peptidyl analogues) may have improved properties (e.g., decreased proteolysis, increased retention or increased bioavailability). It should be noted that peptidomimetics may or may not have similar two-dimensional chemical structures, but share common three-dimensional structural features and geometry. Each peptidomimetic may further have one or more unique additional binding elements.

The hybrid nanopore structure, as defined herein, may be prepared by a process comprising contacting a solid substrate having at least one nanopore perforated therethrough with at least one ring-like polypeptide under conditions permitting placement of said at least one ring-like polypeptide at the rim opening of said at least one nanopore or in an interior region of said at least one nanopore.

In some embodiments, the hybrid structure is formed by self-assembly. In some embodiments, the formation of the hybrid structure is driven by application of voltage.

As shown in Example 2 herein below, and specifically in FIG. 2A, addition of SP1 to a solid substrate resulted in trapping of SP1 onto the nanopore rim as indicted by the distinct three peaks. Further, as shown in FIGS. 2B to 2D, arrangement of SP1 was found to be in an orientation that was essentially parallel to the nanopore planar orientation. The trapping (coating) of SP1 in the nanopore was found to be reversible and depended on the applied polarity.

As further shown in Example 2, specifically in FIGS. 2G and 2H, the trapping of the SP1 in the nanopore may be affected by the SP1 characteristics. For example, different derivatives of SP1 were found to have different trapping behavior. Specifically, in an SP1 mutant, SiSP1, a lower voltage was required in order to trap the polypeptide in the nanopore.

The hybrid structure may be part of a device, e.g., an electronic device. The electronic device may comprise a measuring unit.

Thus, in some embodiments, the present invention provides a device comprising (i) a hybrid structure as defined herein and (ii) a measuring unit.

According to some embodiments, the hybrid structure is placed within the device such that it may separate two chambers. The two chambers may be held in place separately. In some embodiments, and as described herein below, the two chambers may be connected electrically only by the electrolyte solution. The chambers as described herein may be prepared by any conventional material known in the art to be suitable for such a purpose. Non-limiting examples include polydimethylsiloxane (PDMS), plastic, teflon and any known insolating solid material. In some embodiments, the chambers comprise an electrolyte solution.

The device described herein may comprise an electrode assembly constructed of a set of at least two electrodes. In some embodiments, each chamber is equipped with an electrode or an electrode assembly. In some embodiments, the electrode is an Ag/AgCl electrode.

As noted above, the at least one ring-like polypeptide is not limited to any polypeptide and may be for example SP1 as defined herein. In some embodiments, the device is configured such that the bottom of one of the two separated chambers faces (in connection with, touching upon) the first surface (with the SP1) and comprising the opening of the nanopore in the first surface. In some embodiments, this is referred as the cis chamber (or cis reservoir).

In some embodiments, the chamber facing the first surface has an opening of between about 1 nm to about 10 nm; in some other embodiments, between about 2 nm to about 5 nm; in some further embodiments, between about 3 nm to about 4 nm. The opening is on top of the hybrid structure such that it covers the nanopore diameter. The opening in the chamber may be of any shape for example a funnel shape aperture. The opening in the chamber may be aligned with the hybrid nanopore by any known method in the art, for example by an optical microscope.

In some other embodiments, the top of one of the two separated chambers faces (in connection with, touching upon) the second opposite surface and comprising the opening of the nanopore in the second surface. In some embodiments, this is referred as the trans chamber (or trans reservoir).

In some embodiments and specifically when the chambers are filled with an electrolyte solution, flow of solution may be permitted through the nanopore from the first opening to the second opening via the interior of the nanopore. Thus, the two separate chambers are in liquid or gas communication.

In some embodiments, the device comprises a microfluidic system enabling changing sample solution. In some embodiments, the device comprises a cooling-heating system to control the temperature of the device. These systems and any additional system used in the device may be manually or controlled by a computer. In some yet other embodiments, and in order to reduce possible noise, the device may be placed within a Faraday cage and even on top of a vibration isolation table.

The device according with the present disclosure comprises a measuring unit. The measuring unit is adapted to measure ionic current through the nanopore. In some embodiments, the ionic current is generated and measured by the same unit. In some other embodiments, different units are required to generate and measure the current. In some embodiments, the unit may be a voltage source, patch clamp system. In some embodiments, the generating and/or measuring unit may be further equipped with an amplifier and/or a low pass filter and/or digitizer.

In some embodiments, the measuring unit comprises a computer readable system.

The hybrid structure and the device comprising the structure may be used for analyzing a sample when the sample is placed in close proximity to the nanopore or alternatively in the cis chamber and provided that the sample is allowed to pass through the nanopore. The sensitivity and specificity of the hybrid nanopore described herein to monitor translocation of analytes was determined herein.

Generally and as shown herein, when voltage is applied to the hybrid nanopore and no analyte is presented near the nanopore or in the cis chamber, a stable ionic current representing an open pore current may be measured.

When an analyte is added near the nanopore or to the cis chamber near the nanopore, the analyte may pass through the nanopore to the other side of the nanopore (membrane), at time may be the trans chamber. In addition, the analyte may be present near one opening of the nanopore. When the analyte is present near (namely not in the interior) or inside the nanopore (in the interior) (referred herein below also as the monitoring step), part of the ionic flow in the nanopore is changed causing a detectable change in ionic current. The change may be an increase in current or blockade in current. This signal (transient) may be dependent on different parameters for example the properties of the nanopore, electrolyte solution, and the passing molecule. Thus, the hybrid nanopore provides a fundamental tool for sample analysis.

Thus, the present disclosure provides in accordance with its further aspect a method for analysis of at least one analyte in a sample comprising: (a) applying a sample comprising at least one analyte or suspected to comprise at least one analyte onto a hybrid structure, wherein the hybrid structure as defined herein. In accordance with the present disclosure the polypeptide is SP1 polypeptide. The next step (b) comprises permitting the sample to flow through the nanopore. In the subsequent step (c), a determination is made of at least one of (i) presence or absence of an analyte in the sample, (ii) identity of the analyte in the sample, and (iii) concentration of the analyte in the sample.

In accordance with the method described herein, the sample comprising at least one analyte or suspected to comprise at least one analyte may be mixed with SP1 and then applied onto the solid nanopore.

The method may further comprise monitoring at least one measurable parameter related to the nanopore that may be indicative inter alia of the passing of an analyte through the pore and thus permit the determination step (c).

In some embodiments, at least one measurable parameter is a chemical or a physical parameter. In some further embodiments and as detailed herein below, the at least one measurable parameter is an optical parameter. In some embodiments, the measurable parameter is an electrical signal.

Several measurable parameters may be obtained when an analyte is near or in a hybrid nanopore. In some embodiments, a change in the current (or the current value) may be detected.

As used herein, the "change in the current value" may be determined (measured) by comparing an observed current to a current measured at an earlier time point, e.g., in the absence of a sample, and determining the ratio of the values between the two measurements. The change in the current may be either a blockage or an increase in the current. In some embodiments, a blockage (drop) in the current may be observed and, e.g., subsequently compared to a previous measurement.

In some embodiments, the change in current may be expressed as the fraction or percentage of the open nanopore current, open channel current, $I/I_o$, where $I$ is the blockade current and $I_o$ is the open channel current (e.g., in case an analyte is not detected). In some embodiments, the current blockade as noted above may indicate that an analyte is present at a region proximal to hybrid nanopore or in the nanopore structure, e.g., during passage through the hybrid nanopore channel.

In some embodiments, the change in current may be defined as an event having measurable time duration. The time duration of the change in the current or the time duration of a measurable or observed or detected event refers to the period over which the change in current occurs (measurable in millisecond, seconds, etc). In some embodiments, the measured time of the change (event) may reflect on the translocation time (passing) of a sample or an analyte, as defined herein, through the hybrid structure.

In some embodiments, the period over which the change in the current occurs may be determined as the time difference between a time point when a first current change (increase or blockage) is observed and a later time point when the change is arrested or further altered. In some embodiments, the time period is measured until a further change in the blockage or increase in the current is observed. This may be usually determined over a threshold value that is set beyond the baseline noise level.

In some embodiments, the time duration of the change may be fitted by Gaussian. In some other embodiments, the time duration of the change may be fitted by exponential with time constant.

In some other embodiments, the events are represented by transient spikes (indicative of one or more change in a measurable current). In some other embodiments, the frequency of current change events may be determined.

In some embodiments, the event integral, as described herein may be determined by calculating the integral of ionic current over the duration of an event.

In some embodiments, the at least one measurable parameter is at least one of (i) change in current, and (ii) time duration of a change in the current and any combination thereof.

When referring to electric current it should be noted to encompass electric current either in a direction parallel to the surface of the solid membrane; or tunneling current perpendicular to the surface.

In some embodiments, the at least one parameter may be determined manually by visual inspection or by automated means or any combination of the two. In some embodiments, automated means including computational analysis may be used, for example by application of appropriate algorithms.

In some embodiments, the at least one measured parameter may be used to obtain at least one data value related to the at least one parameter.

In some embodiments the method comprise comparing the at least one measurable parameter and/or the at least one data value with a predetermined standard corresponding parameter and/or corresponding data value. This may be done by referring to known measurements or to experiments wherein no measurement is done prior to application of the sample to be tested.

In some other embodiments, the method comprises comparing the at least one measurable parameter and/or the at least one data value with a corresponding parameter and/or corresponding data value obtained in a control study the absence of a sample before application of a sample.

As used herein the term "comparing" denotes any examination of the at least one measurable parameter and/or the at least one data value obtained in the samples as detailed throughout in order to discover similarities or differences between at least two different samples. It should be noted that comparing according to the present invention encompasses the possibility to use a computer based approach.

The present method disclosed herein also comprises steps performed prior to application of the sample to be tested onto the hybrid structure. In some embodiments, the method further comprises filling the two separate chambers, the cis chamber and trans chamber with an electrolyte solution. In some embodiments, the solution is a standard solution, for example comprising 1 M KCl TE (10 mM tris and 1 mM EDTA at pH 7.4) buffer solution. In some other embodiments, after filling the chambers with the electrolyte solution, initial testing of the nanopore is performed, for example such as nanopore conductivity testing. In some further embodiments, these initial measurements may be used to determine at least one measurable parameter related to the nanopore possibly to determine data value obtained in the absence of a sample. In some further embodiments, voltage is applied to the electrodes and the current of the nanopore is determined in the absence of a sample, to obtain the open channel current (also referred herein as the open nanopore current).

In connection with the present disclosure, the sample is applied onto the hybrid nanopore. Application of the sample may be by any method known in the filed for example pouring, injecting and others, enabling the sample to be in close proximity and in physical contact to one opening of the nanopore.

In some embodiments, the sample is applied onto the hybrid nanopore, as such the sample is applied to the nanopore's opening comprising the SP1 polypeptide. In some specific embodiments, the sample is applied onto the first opening of the hybrid nanopore within the first surface of the membrane.

In some embodiments, the sample comprising the SP1 is applied onto the nanopore (with no SP1 or with partial SP1 coating). In some specific embodiments, the sample is applied onto the first opening of the nanopore within the first surface of the membrane.

The sample is then permitted to pass through the nanopore. In the context of the present disclosure, passing of a sample through the nanopore enables measuring at least one measurable parameter related to the nanopore. In some embodiments, the at least one measurable parameters may be at least one physical or chemical property. In some other embodiments, the at least one measurable parameters may be at least one optical property.

Without being bound by theory, it is suggested that in case an analyte is present in the sample, it will induce a change in at least one of the measured parameters (measurable parameter). Further, and without being bound by theory, in case an analyte is not present in the sample, no change in the at least one parameter is induced. More specifically, no change in the current is detected.

Generally, when used, the term "change" or "difference" of at least one parameter relates to an increase or decrease in at least one parameter as described herein. More specifically, a reduction in the current is by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 300%, 400%, 500%, 600%, 700%, 800%, 900% or about 1000% as compared to corresponding current in a control measurement (at times open nanopore current).

In some embodiments, the method provides a qualitative (yes=presence, no=absence) result by comparison with a control measurement as described herein. It is to be understood that the term "absence" in the context of the assay also encompasses presence of the analyte in an amount that is lower than the detection limit of the method.

The "sample" according to the present invention may be any sample including, but not limited to, biological samples obtained from biological systems (including cell cultures, micro-organism cultures), biological samples obtained from subjects (including humans and animals), samples obtained from the environment for example soil samples, water samples, agriculture samples (including plant and crop samples), food samples. The term "sample" may also include body fluids such as whole blood sample, blood cells, bone marrow, lymph fluid, serum, plasma, urine, sputum, saliva, faeces, semen, spinal fluid or CSF, the external secretions of the skin, respiratory, intestinal, and genitourinary tracts, tears, milk, any human organ or tissue, any biopsy, for example, lymph node or spleen biopsies, any sample taken from any tissue or tissue extract, any sample obtained by lavage optionally of the breast ductal system, plural effusion, samples of in vitro or ex vivo cell culture and cell culture constituents.

In some embodiments, the sample is a liquid sample. In some embodiments, the liquid sample is liquid in its natural state. In some further embodiments, the liquid sample is pre-treated to be in a liquid state. Pre-treatment may be by any method that changes a sample that is not liquid in its natural state into a liquid state. In some embodiments, pre-treatment is by extraction. In some other embodiments, the sample comprises at least one liquid fraction.

Depending on the specific method and results to be obtained, the sample in the context of the invention may be prepared prior to the analysis in in vitro settings and not necessarily obtained from a subject.

The term "analyte" as used herein denotes a molecule or an ion which may be found in a sample, and which detection or quantification is required. In some embodiments, the sample may comprise a binding agent capable of binding to the analyte prior to or during passing through the nanopore (or hybrid nanopore). The term "binding agent" as used herein refers to any molecule capable of specifically binding to the analyte for example an aptamer, an antibody, a receptor ligand or a molecular imprinted polymer.

In some embodiments, the analyte may be a protein, a polypeptide, a peptide, a ganglioside, a lipid, a phospholipid, a carbohydrate, a small molecule or a nucleic acid.

Non-limiting examples in accordance with the invention are soluble cancer markers, inflammation-associated markers, hormones, cytokines, drugs, and soluble molecules derived from a virus, a bacteria or a fungus for example, toxins or allergens.

In some embodiments, the analyte is a cancer (or tumor) marker or a viral marker (or any fragment thereof). In general, a tumor marker may be found in the body fluids such as in blood or urine, or in body tissues. Tumor markers may be expressed or over expressed in cancer and are generally indicative of a particular disease process.

In some embodiments, the analyte is a nucleic acid.

In some embodiments, the analyte may be modified. In some embodiments, the analyte may be conjugated (chemically) to a moiety that may be any compound capable of producing a detectable signal. The moiety may be for example a chromophore, a fluorophore or a luminancephore. In some other embodiments, the at least one measurable parameter may be an optical signal. As appreciated, Alkaline Phosphatase (AP) or Horse Radish Peroxidase (HRP) substrate detection may be achieved by chromatic signal, fluorescence signal or luminescence signal, which may be detected using various spectrophotometers and fluorometers.

In accordance with the present invention and as disclosed herein below, the analyte may be a nucleic acid molecule and in some embodiments of the present disclosure a modified nucleic acid molecule.

As shown in Example 3 herein, ds-DNA translocated through the nanopore. Interestingly, the ds-DNA passing through the hybrid nanopore adopts a linear confirmation as compared to the bare nanopore (no SP1). Further interestingly, translocation through the nanopore was found to slower as compared to the bare nanopore as indicated by the longer dwell time.

Without being bound by theory, it is suggested that the positive charges that are present in the inner pore of the SP1, may electrostatically interact with the negatively charged DNA when translocated through it and as such slow down the DNA translocation. Previous studies showed that DNA translocation through this hybrid structure was found to be the same as when the α-hemolysin is buried in the less stable lipid bilayer. Namely, no advantage was observed to the hybrid nanopore. As such, the results shown here are superior to the data found in the art.

An improvement of the translocation temporal resolution to few nucleotides per ms surprisingly shown herein is highly advantage and paves the way to a new arena of using hybrid nanopore with SP1 for nucleic acid sequencing. Further, the selectivity of the hybrid nanopore disclosed herein for linear conformation is almost essential for sequencing the translocated nucleotides.

Thus, in accordance with another aspect, the present disclosure provides a method for sequencing a nucleic acid molecule comprising (a) applying a sample comprising at least one nucleic acid molecule onto a hybrid structure, and determining the sequence of the nucleic acid molecule.

As used herein, "nucleic acid(s)" is interchangeable with the term "polynucleotide(s)" and generally refers to any polyribonucleotide or poly-deoxyribonucleotide, which may be unmodified RNA or DNA or modified RNA or DNA or any combination thereof. "Nucleic acids" include, without limitation, single- and double-stranded nucleic acids.

As used herein, the term "nucleic acid(s)" also includes DNAs or RNAs as described herein that may contain one or more modified bases. Thus, DNAs or RNAs with backbones modified for stability or for other reasons are "nucleic acids". The term "nucleic acids" as it is used herein embraces such chemically, enzymatically or metabolically modified forms of nucleic acids, as well as the chemical forms of DNA and RNA characteristic of viruses and cells, including for example, simple and complex cells. A "nucleic acid" or "nucleic acid sequence" may also include regions of single- or double-stranded RNA or DNA or any combinations.

In some embodiments, the nucleic acid is DNA. In some other embodiments, the nucleic acid is RNA. In some embodiments, the nucleic acid is a double stranded (ds) nucleic acid. In some other embodiments, the nucleic acid is a single stranded (ss) nucleic acid.

When referring to sequencing of at least one nucleic acid molecule, it should be noted that the molecule may be a ds-DNA, ss-DNA, ds-RNA or ss-RNA. The nucleic acid may be a synthetic molecule or alternatively a nucleic acid molecule obtained from any biological sample, food sample or the like as described herein. In some embodiments, the nucleic acid subjected to analysis is in a linear conformation. In some further embodiments, the nucleic acid is an unstructured nucleic acid.

As noted herein, the nucleic acid may be a modified nucleic acid. In some embodiments, the nucleic acid molecule contains 2-aminoadenosine, 2-thiothymidine, inosine, and pyrrolopyrimidine. In accordance with some other embodiments, the nucleic acid molecule may be attached to a fluorescent moiety. In accordance with some further embodiments the nucleic acid is biotinylated. As appreciated, modification of a nucleic acid as described herein may be by covalent bonding. The terms "conjugation", "association", "connection", "interactions" are used interchangeably to denote a bonding between two chemical entities. The bonding may be for example covalent binding, hydrogen binding, electrostatic binding, hydrophobic interactions and the like.

In some embodiments, the conformation of a nucleic acid molecule can be evaluated by the blockage of the current. As shown herein, translocation of a nucleic acid in a linear conformation has a distinct pattern that differs from translocation of a variety of conformations.

In some other embodiments, the number of bases (also termed herein nucleotides) or the size of a DNA molecule can be estimated from the integrated area of an event. In some further embodiments, a linear nucleic acid molecule can be used as a marker.

In the context of the present disclosure evaluation of the nucleic acid conformation and the nucleic acid size may be determined for example by recording events from a known nucleic acid (ladder) molecule, washing the known molecule and adding a tested molecule.

As appreciated, detection of modified nucleic acid may be for example by optical means such as fluorescence.

In some embodiments, in case the nucleic acid is ss-DNA or ss-RNA, the complementary strand may be formed prior to or during passing through the nanopore. In such embodiments, the method further comprises providing a suitable enzyme such as polymerase or exonuclease.

Sequencing of a nucleic acid molecule involves determining the precise order of nucleotides (also denoted herein as bases) within a nucleic acid molecule, namely, determine the order of the four bases: adenine, guanine, cytosine, and thymine in a strand of DNA or adenine, guanine, cytosine, and uracil in a strand of RNA.

In the context of the present disclosure, the sequencing method comprises passing of the nucleic acid molecule through the nanopore from one opening to the opposite opening in a sequential nucleotide-by-nucleotide translocation. The information of each nucleotide is monitored separately in a monitoring step. In some embodiments, the monitoring step comprises determining at least one measurable parameter related to a nucleotide to possibly obtain a data value. The at least one measurable parameter and/or the at least one data value may be indicative of a nucleotide. The at least one measurable parameter and/or data value is further compared to a corresponding predetermined standard parameter and/or corresponding data value or to a corresponding predetermined standard parameter and/or corresponding data value obtained from a control nucleotide.

In some embodiments, the at least one measurable parameter and/or data value obtained at each monitoring step is compared to a predetermined standard parameter or data value of a nucleotides in a control sample. The resemblance of the at least one parameter or data value obtained at each monitoring step to at least one parameter or data value obtained for any one of the different nucleotides in a control sample is calculated in order to determine the nucleotide within the nucleic acid molecule. The degree of resemblance is indicative of an existence of a specific nucleotide in the nucleic acid molecule.

As such, the method according to some embodiments provides a qualitative test by providing the analysis of the identity of the analyte and in some embodiments, the identity of the specific nucleotide within the nucleic acid molecule.

In another aspect, the present invention provides a method for the diagnosis of a condition in a subject comprising using an analysis method in accordance with the invention as described above. In some embodiments, the analyte is an analyte associated with the condition and wherein the presence or absence of analyte is indicative of the presence of a condition in the subject.

In another aspect, the present invention provides a method for monitoring the efficiency of a therapeutic regimen in a subject suffering from a condition comprising using an analysis method in accordance with the invention as described above. In some embodiments, the analyte is associated with the condition and wherein the amount of analyte is indicative of the level of the condition and thereby of the efficiency of the therapeutic regimen in the subject.

In some embodiments, a sample is obtained from a subject and is subsequently subjected to a method according to the invention.

As used herein, "disease", "disorder", "condition" and the like, as they relate to a subject's health, are used interchangeably and have meanings ascribed to each and all such terms. In some embodiments, the condition is a pathological condition.

The "pathological condition" according to the present invention may be selected from but not limited to cancer, inflammation, blood coagulation disorders, and autoimmunity. Accordingly, the method of the invention may be used in the detection of known cancer markers, markers of inflammation, such as procalcitonin which is a known marker for sepsis, peptides such as penicillin-binding protein 2 (PBP2), kinesin spindle protein (KSP), toxins and allergens.

In some other embodiments, the pathological condition is a viral, bacterial or fungal infection. Non-limiting examples of viral infection comprises *Hepatitis* B virus (HBV), *hepatitis* C virus (HCV), Cytomegalovirus (CMV), Human immunodeficiency virus (HIV), Epstein-Barr virus (EBV), HERPES virus, Polio virus, and influenza virus.

Non-limiting examples of bacterial infection comprises *Listeria, Diphtheria, E. coli*, Group B *streptococcus* (GBS), Group A *streptococcus, Tuberculosis* (TB), *Salmonella, Vibrio Cholerae, Campylobacter, Brucellosis,* meningococcus, *Streptococcus pneumonia* and *Candida*.

In some embodiments, the pathological condition is cancer. Cancer is interchangeably used with the terms malignancy, tumor and is referred to herein as a class of diseases in which a group of cells display uncontrolled growth and invasion that may destroy adjacent tissues, and sometimes leads to metastasis (spreading to other locations in the body). Cancer may be a solid cancer or a non-solid cancer and may be classified as carcinoma, sarcoma, lymphoma, leukemia, germ cell tumor, or blastoma.

In some further embodiments, the pathological condition is an autoimmune disease. As appreciated in the art, autoimmune diseases arise from an overactive immune response of the body against substances and tissues normally present in the body. Non limiting examples of autoimmune disease are Multiple sclerosis, Arthritis, Autoimmune hepatitis, Crohn's disease, Diabetes mellitus type 1, Inflammatory bowel disease, Multiple sclerosis, Psoriasis, Rheumatoid arthritis, Wegener's granulomatosis.

Using the detection methods of the present invention the level of target molecules indicative of the pathological state may be determined. Therefore, the measurement of the levels of these target molecules can serve to diagnose the pathological condition, to monitor disease progression and to monitor efficacy of a therapeutic regiment, i.e. monitor the response of the subject to treatment.

In some further embodiments, the condition is a non-pathological condition.

Other aspects of the present invention provide use of the hybrid structure as disclosed herein in the manufacture of a device according to the invention.

In some other aspects, there is provided a hybrid structure and/or device comprising same for use in research purposes. Non-limiting examples include laboratory use, scientific experiments and the like.

In some further aspect, there is provided a hybrid structure and/or device comprising same for use in analysis of at least one analyte in a sample. In some embodiments, the hybrid structure is used in determining at least one of (i) presence or absence of an analyte in the sample, (ii) identity of the analyte in the sample, (iii) concentration of the analyte in the sample.

In accordance with the present disclosure, the hybrid structure is used in sequencing a nucleic acid molecule The term "about" as used herein indicates values that may deviate up to 1 percent, more specifically 5 percent, more specifically 10 percent, more specifically 15 percent, and in some cases up to 20 percent higher or lower than the value referred to, the deviation range including integer values, and, if applicable, non-integer values as well, constituting a continuous range.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 1A-1D show SP1 translocation through solid nanopores.

FIG. 1A is a schematic illustration of translocation of SP1 through a 15 nm solid-state nanopore in a SiN membrane (shown in the TEM image, the scale bar is 5 nm) separated between two reservoirs with a potential difference.

FIG. 1B shows four consecutive current versus time traces of SP1 (concentration is 10 mg/mL) translocation through the solid-state nanopore at various voltages, translocation events were represented by transient spikes, inset is a control experiment after diluting the protein concentration, showing lower translocation events rate.

FIG. 1C is a graph showing the events rate dependence on the applied voltage with a logarithmic behavior. The dashed line showed a linear fitting (in log scale) to the experimental data (dots with error bars from at least 3 repetitions) at various voltages.

FIG. 1D shows SP1 translocation trace demonstrating the negative charge nature of the SP1, where translocation events were only observed at positive polarity.

FIGS. 2A-2I show SP1 trapping on a solid nanopore.

FIG. 2A is a cartoon illustrating trapping of SP1 on top of a solid nanopore of 3 nm (smaller than the protein/polypeptide size), scale bar in the TEM image is 5 nm, the typical trace of successful SP1 trapping on the pore above shows three distinct peaks in the current histogram, which represent open pore without protein (1), landing of protein on the pore (2), and final trapping (3), respectively at 400 mV.

FIGS. 2B-2D are traces of SP1 trapping in nanopores with various diameters (3 nm 5 nm and 8 nm, respectively) at 400 mV, with the baseline current rises as the nanopore diameter increases. The scale bar for the TEM images is 5 nm.

FIG. 2E is a graph showing the dependence of the current reduction (ratio between current drop and baseline current) of the trapping events (current drop longer than 1 s is defined as an SP1 trapping event) on the pore diameter measured for nanopores with 3, 5 and 8 nm diameter. Inset: shows the conductance model of nanopore taking the geometrical shape into account. The theoretical blocking values are based on the circumstances of SP1 sitting on top of the pore (dots).

FIG. 2F shows traces of SP1 protein trapped on the nanopore and released by manually changing the polarity. When the polarity is switched back, another protein can be trapped.

FIG. 2G shows two traces at 200 and 400 mV of the trapping efficiency of the SP1 (L81C) protein on the nanopore (3 nm pore). A 400 mV potential difference is needed to trap the SP1 (L81C) protein.

FIG. 2H shows three traces at 200, 300 and 400 mV indicating an increased trapping efficiency of a silicon-binding SP1 (SiSP1) mutant on the nanopore (5 nm pore). For this mutant a potential difference of 200 mV was sufficient to trap the silicon-binding SP1 protein on the nanopore.

FIG. 2I shows a trace demonstrating that SiSP1 can sometimes still be trapped after changing to negative voltage bias.

FIG. 3A is a cartoon illustrating trapping of SP1 followed by DNA translocation, which reveals the fourth stage caused by DNA translocation through the hybrid pore. A typical trace demonstrates DNA translocation through L81CSP1 nanopore, recorded at 400 mV. The current histogram shows a fourth peak that represents DNA translocation.

FIG. 3B is a graph showing the 48 kbp dsDNA translocations rate through SP1 hybrid nanopore as a function of DNA concentration at 400 mV.

FIGS. 3C and 3D shows insertion of 10 nm gold nanoparticle (GNP) connected by thiol to a 26 bases long ssDNA which is hybridized to another 100 bases long ssDNA, into a hybrid nanopore. FIG. 3C: trapping of SP1 occurs after 1 second, resulting in the first reduction of the current. After adding GNP-DNA conjugates, an insertion of GNP-DNA to the SP1 happens after 158 seconds, resulting in the second reduction of the current to less than 10% of the baseline current. FIG. 3D: GNP-DNA conjugate stays in the SP1 pore for ~1 s. Then, the GNP was released or hybridized 100 bases long ssDNA was dehybridized and GNP released, leading to a recovery of the open SP1 current.

FIGS. 3E and 3F show representative traces of DNA translocation in bare SiN (FIG. 3E) and SP1 nanopores (FIG. 3F). The events detection is done using adaptive threshold method with exclusion of short pulses (<0.1 ms).

FIG. 3G shows a scatter plot and histogram of the dwell time and conductance of 48 kbp DNA translocated through L81SP1 hybrid nanopore (dots) and through bare SiN nanopore (triangles). The conductance histogram shows a narrow peak for DNA translocation through L81SP1 nanopore indicating a single DNA conformation within the L81SP1 with respect to multiple peaks for DNA translocation through the bare SiN nanopore, indicating variable DNA conformations.

FIG. 4A 48 kbp dsDNA translocation dwell time of SP1 hybrid nanopores vs. bare solid state pore. The 400 mV trace was measured for SP1 (L81C) hybrid nanopores and the 100, 200, and 300 mV traces were measured for SiSP1 hybrid nanopores.

FIG. 4B depicts most probable dwell time as a function of voltage. Both panels show the clear slow down of the translocation by the SP1 protein.

DETAILED DESCRIPTION OF EMBODIMENTS

NON-LIMITING EXAMPLES

Methods

Nanopore Fabrication

Figure 1C:
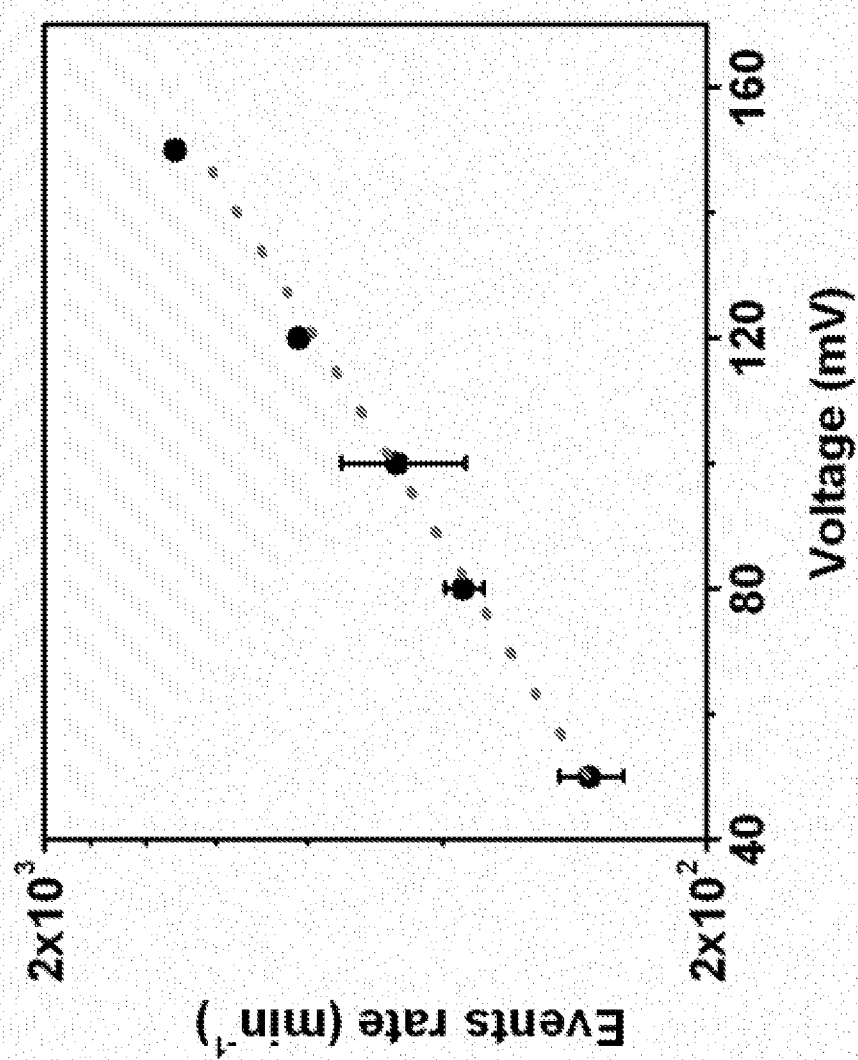

Nanopores were fabricated in 30 nm thick, low-stress SiN windows (50×50 µm$^2$) supported by a silicon chip (Protochips) using a focused electron beam of a 200 keV TEM (Tecnai, F20 G$^2$). Nanopores with small sizes, such as 3-4 nm were made using a shrinkage process by defocusing the electron beam. Once the pores were drilled, they were stored in ethanol:ddH$_2$O (1:1, v:v) immediately to avoid any contamination.

Protein Synthesis

Protein expression, purification and refolding were carried out as described in detail by Heyman et al. Briefly, E. Coli strain BL21(DE3) was used for protein expression, using IPTG (isopropyl β-d-thiogalactopyranoside) as inducer. The protein, which accumulated in inclusion bodies (IBs), was separated by centrifugation, washed, denatured and finally refolded to allow the self-assembly into its dodecamer form. Further purification was conducted using ion-exchange chromatography method. Two types of SP1 mutants were used in this work: L81CSP1 (with no specific binding to Si) and SiSP1 (with specific binding to Si).

The monomer of L81CSP1 is denoted herein as SEQ ID NO:5 and the monomer sequences of the SiSP1 are denoted herein as SEQ ID NO:15 or SEQ ID NO:17.

Translocation Experiments

Nanopore membranes were treated in a Plasma Cleaner for 30 s to facilitate wetting before being mounted in a custom electrophoresis flow cell (Nanopore Solution, Inc.). Two reservoirs on each side with a volume of 1 mL (trans and cis) were filled with filtered and degassed buffer of 1M KCl, 10 mM Tris pH 7.4, 10% Glycerol, and 1 mM EDTA.

A pair of Ag/AgCl pellet electrodes was immersed in the two reservoirs and connected to an Axopatch 200B amplifier (Molecular Devices, Inc.) to record ionic current flow through the nanopore. The whole setup was put in a double Faraday cage to lower external electrostatic interference. Signals were collected at 100 kHz sampling rate using a Digidata 1440A (Molecular Devices, Inc.) and filtered at 10 kHz using the built-in low pass Bessel filter of Axopatch. Clampfit 10.2 (Molecular Devices, Inc.) was used for event detection with an adaptive threshold method, by which short pulses (<0.01 ms) are excluded. All the DNA samples were purchased from Fermentas, Inc. and used as received. The DNA and the SP1 were injected into the cis-side, which is connected to the ground electrode, with a pipette and mixed well by repeatedly sucking and injecting with the pipette.

Results

Example 1

Translocation of SP1 Through Nanopores

This example describes characterization of the translocation nature of SP1 through nanopores. The SP1 has a net charge of −6 charge units per monomer that are distributed on its surface.

FIG. 1A illustrates a pore, slightly larger than the SP1 protein diameter, in a SiN membrane, that separates two ionic buffer reservoirs equipped with a pair of electrodes with a potential difference.

The protein translocation was detected by measuring the transient current blockage (on the time scale of microsecond to millisecond) when the protein was passing through a single nanopore under electrophoretic force. FIG. 1B shows four consecutive 1 min traces at four different voltages (20, 50, 80, and 100 mV). An increased frequency of events was observed upon voltage raising, corresponding to an increased translocation events rate, as expected when increasing the ionic current and force acting on the charged proteins.

The observed rates at 20, 50, 80, and 100 mV were 51, 290±33, 465±32, 587±125 min$^{-1}$, respectively. According to previous studies, the capture rate of polymers threading through a confined hole should follow an exponential increase with increasing voltage, represented by the Van't Hoff-Arrhenius relationship, $R_{capture} \propto e^V$.

This experimental data obtained from 50 mV to 150 mV fitted this relationship (FIG. 1C). At 20 mV the translocation rate did not follow the above equation and was down shifted. It was thus suggested that at 20 mV, the translocation might be dominated by diffusion. As can be seen in FIG. 1B (inset), dilution of the SP1 concentration led to deceased rate.

Figure 1D:
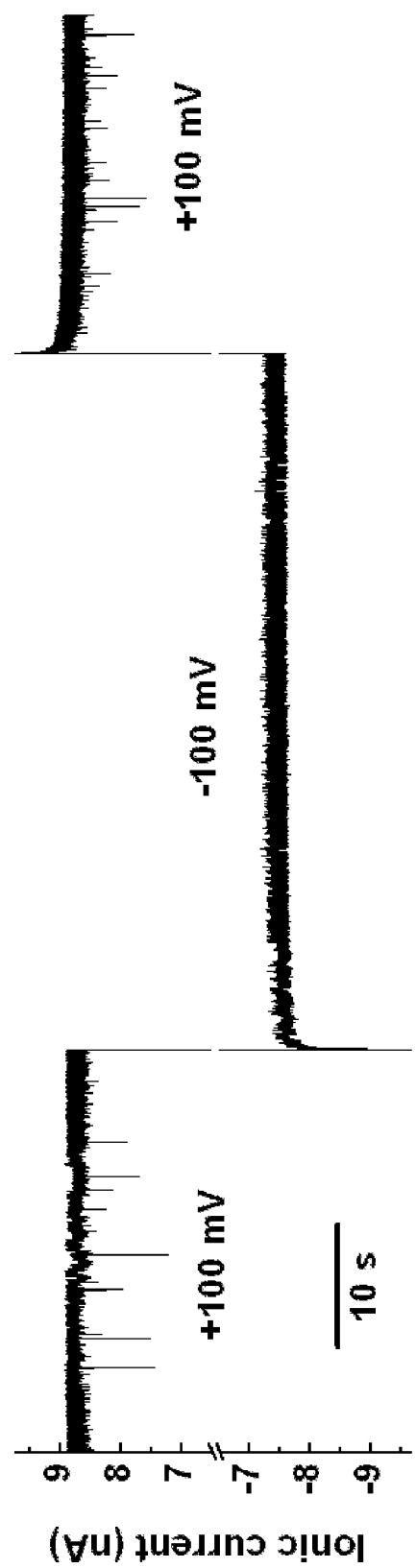

In addition, SP1 translocation events were not observed when the polarity was changed to negative bias but returned after it was changed back to positive bias (FIG. 1D). This suggested that SP1 is negatively charged under these buffer conditions (1M KCl, pH 7.4) and was moved to the nanopore and translocated through it upon positive bias application. This observation was consistent with the fact that the isoelectric point (pI) of the SP1 protein is 4.7.

The voltage and concentration dependence of the translocation confirm SP1 translocation through the nanopore and consequently also the ability to bring the SP1 to the nanopore by dielectrophoresis.

Example 2

Trapping of SP1 in Nanopores

Figure 2A:
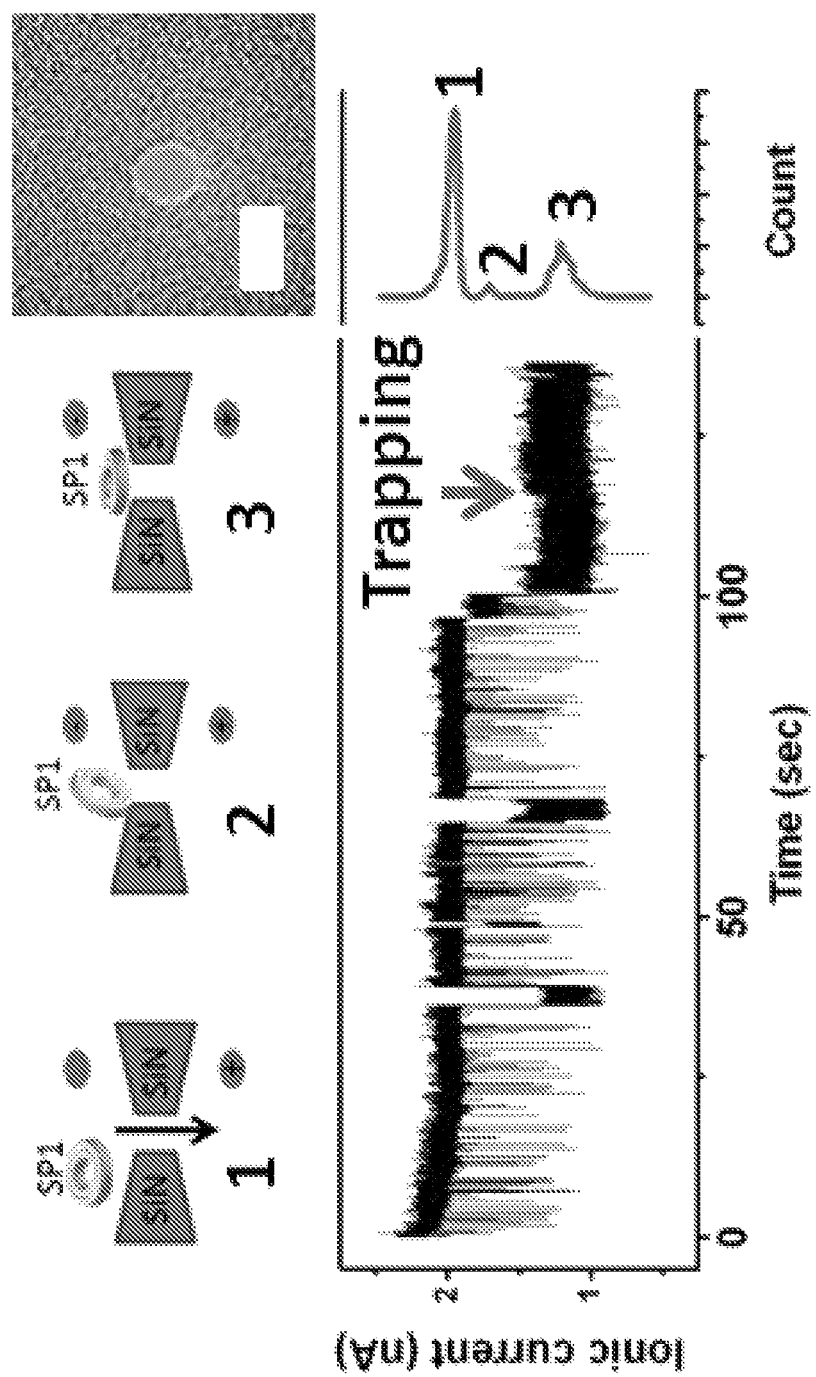

To trap SP1 on the nanopore, 3 nm to 8 nm diameter nanopores (mostly 3 nm to 5 nm) (16 pores) were used (FIG. 2A). The trace in FIG. 2A demonstrated a typical trapping process, which includes three consecutive steps, manifested by three distinct peaks in the current histogram provided on the right side of the trace.

These peaks were interpreted as follows: Initially, there were many events that reflected SP1 hitting on the nanopore, appearing as spikes on the baseline (peak 1). These were followed by an intermediate blockage, possibly in some tilted protein orientations (peak 2), and eventually by a successful trapping (peak 3) in an orientation parallel to the membrane surface.

DNA translocation through the SP1, shown later, was unlikely in non-planar SP1 orientation as the 3 nm width of the "doughnut-shape" SP1 would totally block the 3 nm nanopore opening and not enable dsDNA translocation.

A simple equivalent electric circuit assumed that the SP1 pore introduced a constant serial resistance to the ionic current in addition to the SiN pore resistance. Based on this model, the relative current reduction after trapping should show a strong dependence on the pore diameter. The experimental data fitted well with the calculated current drop assuming that SP1 was indeed sitting on top of the nanopore (FIGS. 2B-2D).

Figure 2B:
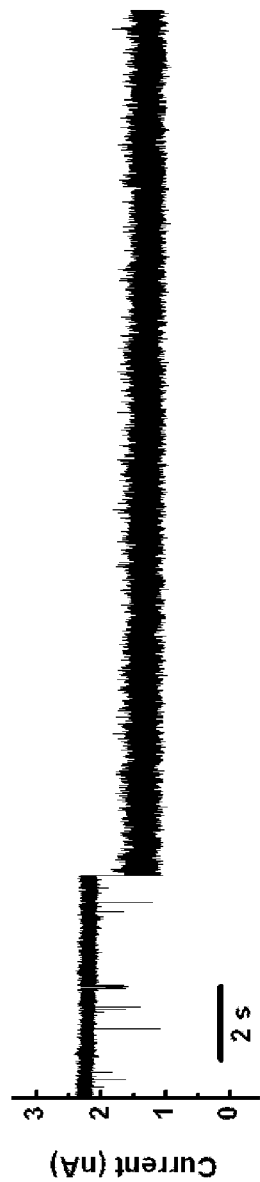
Figure 2B:
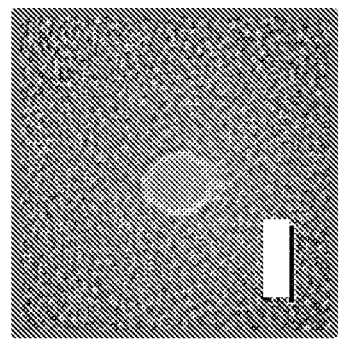
Figure 2E:
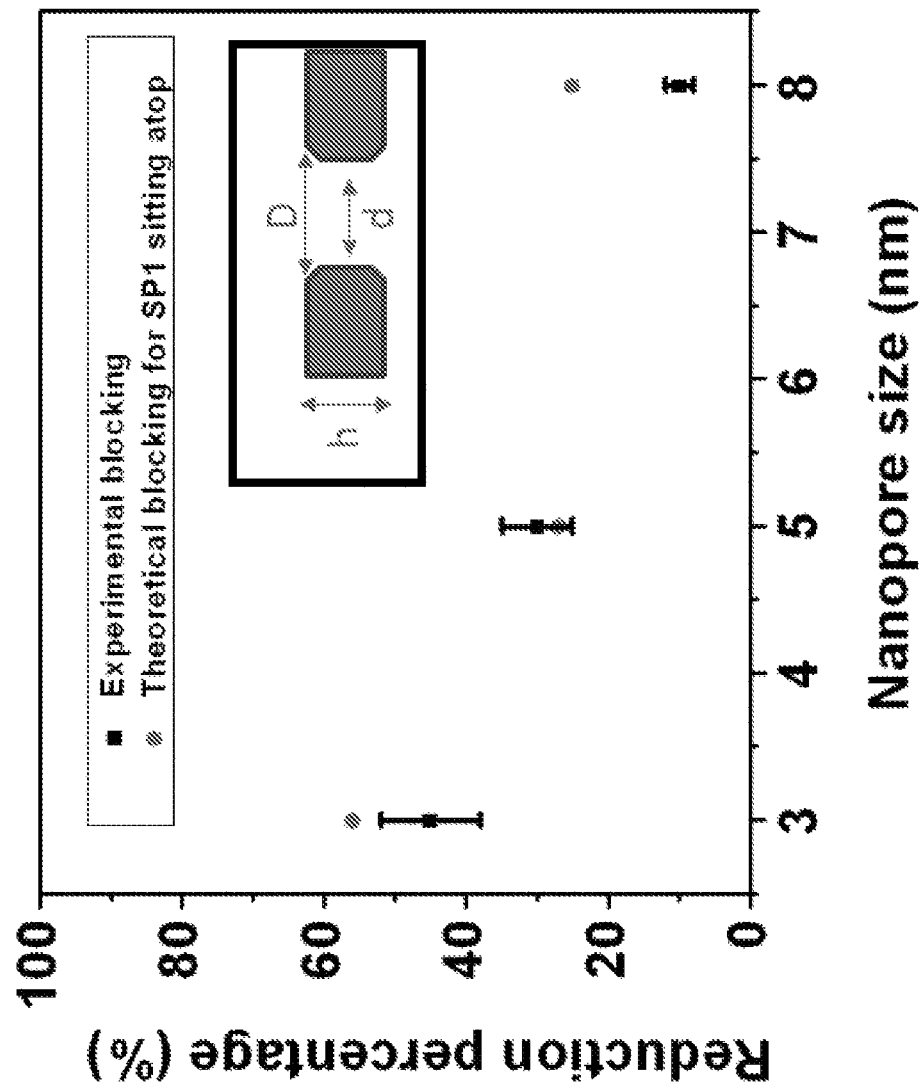

FIGS. 2B-2D indicted that the relative current reduction in a hybrid nanopore, i.e. after SP1 trapping in the nanopore was dependent on the nanopore diameter. The relative current reductions were observed to be 45±7% (5 pores, 30 trapping events), 30±5% (2 pores, 25 trapping events), and 10±2% (2 pores, 15 trapping events) for nanopores with diameters of 3 nm, 5 nm and 8 nm, respectively, as shown in FIG. 2E.

According to the conductance model of nanopore the conductance of the nanopore could be described as $$G = \sigma\left[\frac{4h}{\pi d^2} + \frac{1}{D}\right]^{-1},$$

where h is the thickness of the SiN membrane (30 nm), d is the average diameter of the pore, a is the bulk conductivity of 1 M KCl solution (11.2 S m$^{-1}$), and D is the diameter of the pore opening. The experimental data fitted with the calculated current drop (56%, 27% and 25% for nanopores with diameters of 3, 5 and 8 nm, respectively).

This suggested that SP1 is sitting on top of the nanopore where D and h will be affected by SP1. Thus, the experimental data fitted well with the calculated current drop suggesting that SP1 is sitting atop on the nanopore (FIGS. 2B-2E)

Figure 2F:
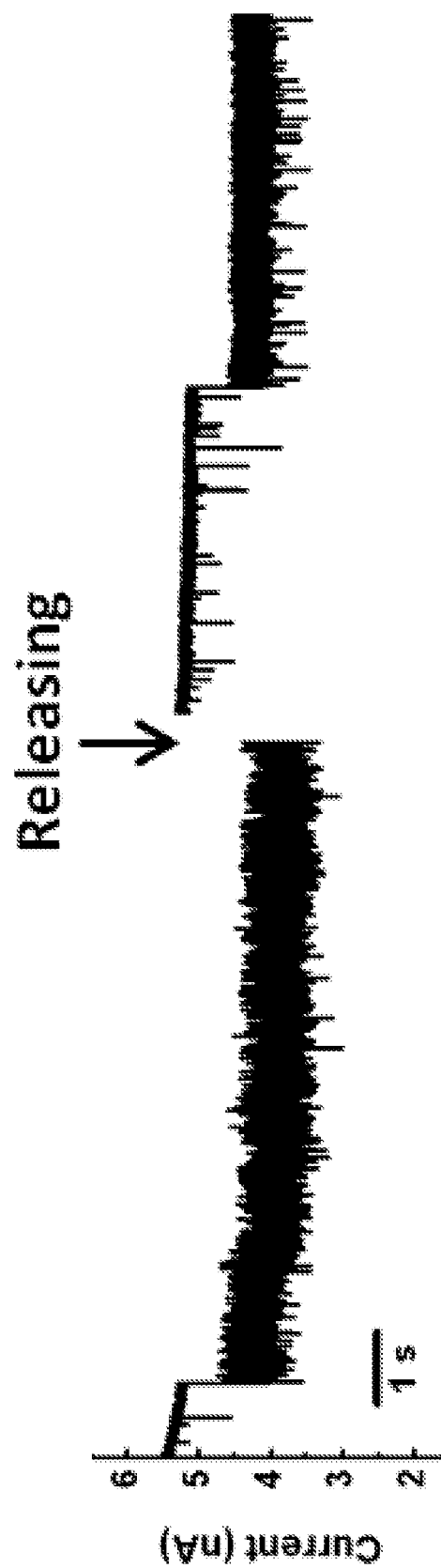

As shown in FIG. 2F, after the SP1 was trapped (left part of the trace), the polarity was changes to intentionally release the SP1 (marked by an arrow) and the baseline went back to the bare pore current level (namely without any protein trapped in the pore).

Thereafter another trapping event took place (right part of the trace). It should be noted that SP1 can be trapped as is, due to its naturally negatively charged surface, namely without any further genetic modifications. This is unlike α-hemolysin that needs was chemically modified for this purpose.

To demonstrate the variability of the trapping behavior and binding affinity to the surface, two SP1 mutants were compared, the first being L81CSP1 (with no specific binding to Si) and the second being SiSP1 that has Si-binding peptide in each N-termini that facilitates binding to Si surfaces.

Figure 2G:
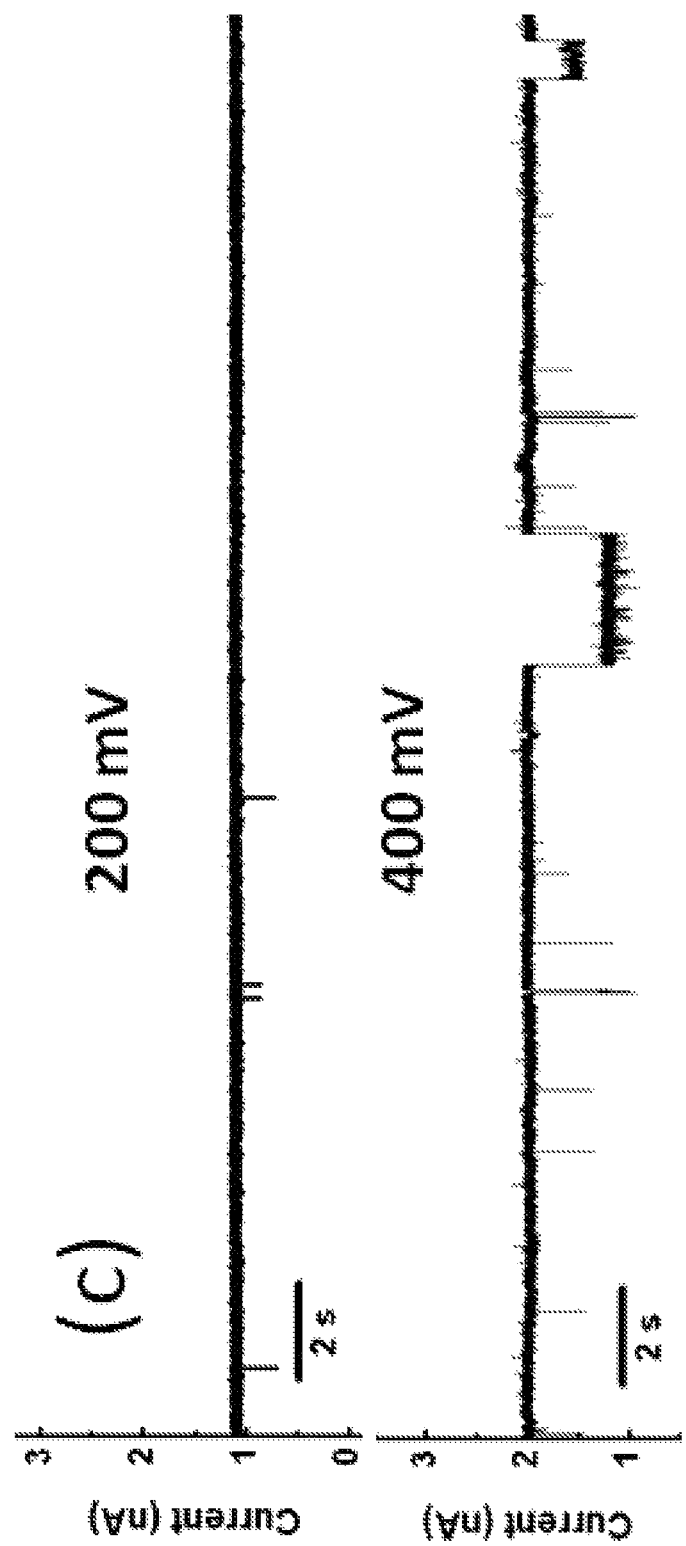
Figure 2H:
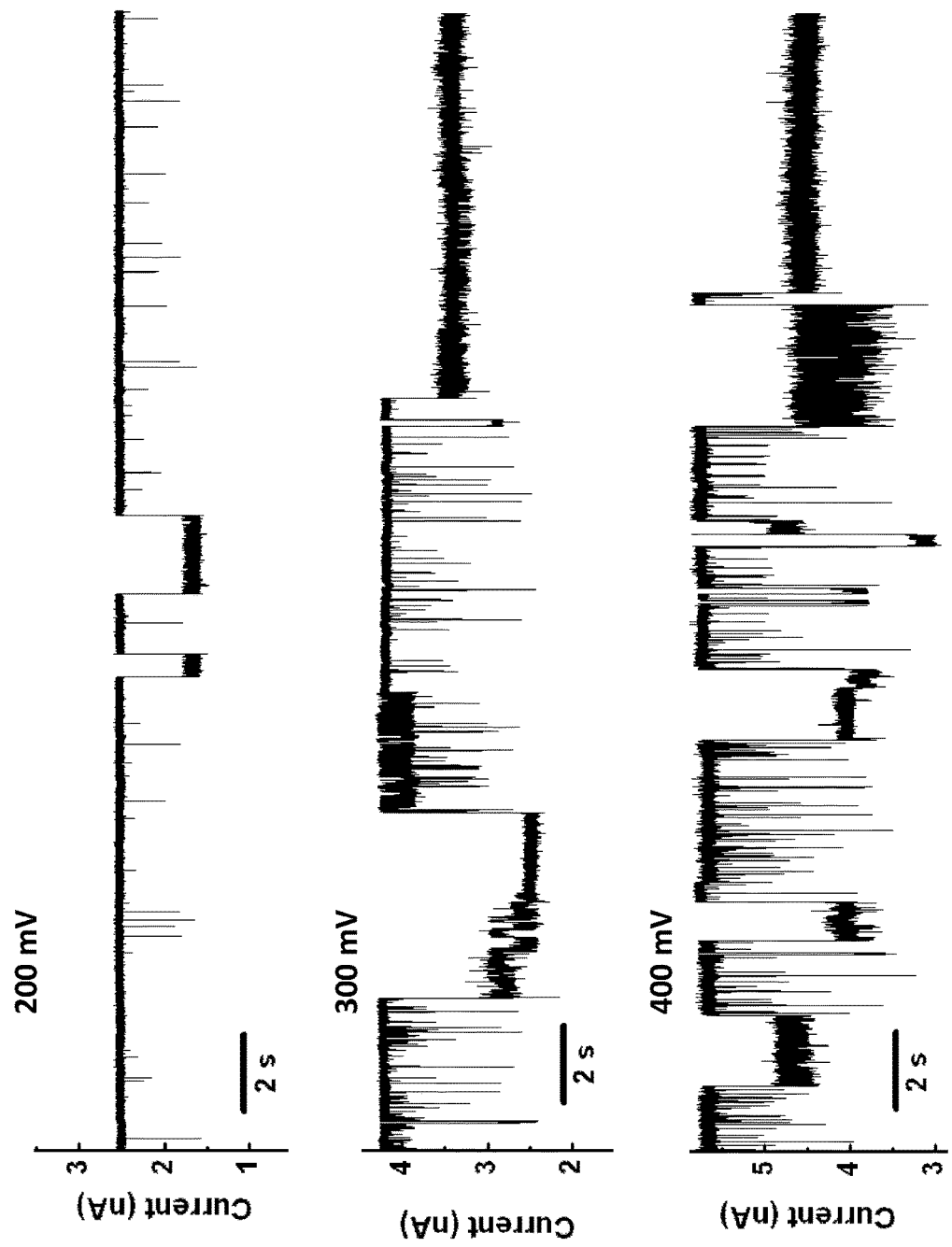

The results are shown in FIGS. 2G and 2H. As can be seen in FIG. 2G, for L81CSP1, the threshold voltage to trap SP1 on the nanopore was 400 mV. At lower potential of 200 mV, no trapping events were detected.

When SiSP1 was used, the trapping threshold was reduced to 200 mV (FIG. 2H). As the voltage rises, the SiSP1 trapping frequency was further increased.

Figure 2I:
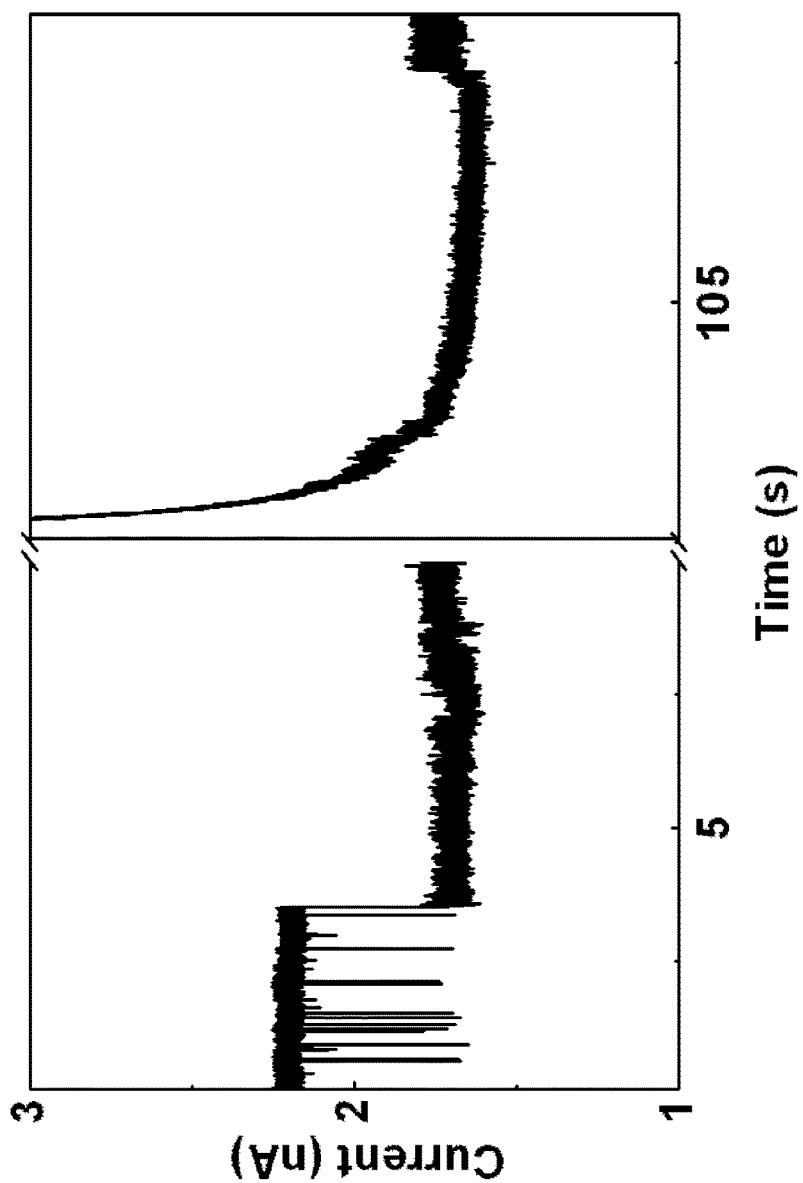

As shown in FIG. 2I, changing polarity failed to release the tightly bound SiSP1 from the nanopore.

Comparison of the two protein mutants showed the influence of the genetically engineered mutations on the protein trapping behavior and further confirms the trapping of the SP1 on top of the nanopore. This was not observed for SP1 with no specific binding, in such case the SP1 was released upon voltage polarity change.

Example 3

Translocation of DNA Through SP1-dressed Nanopores

After characterizing the SP1 trapping, DNA translocation through an SP1-dressed nanopore was demonstrated (FIGS. 3A-3G).

Figure 3A:
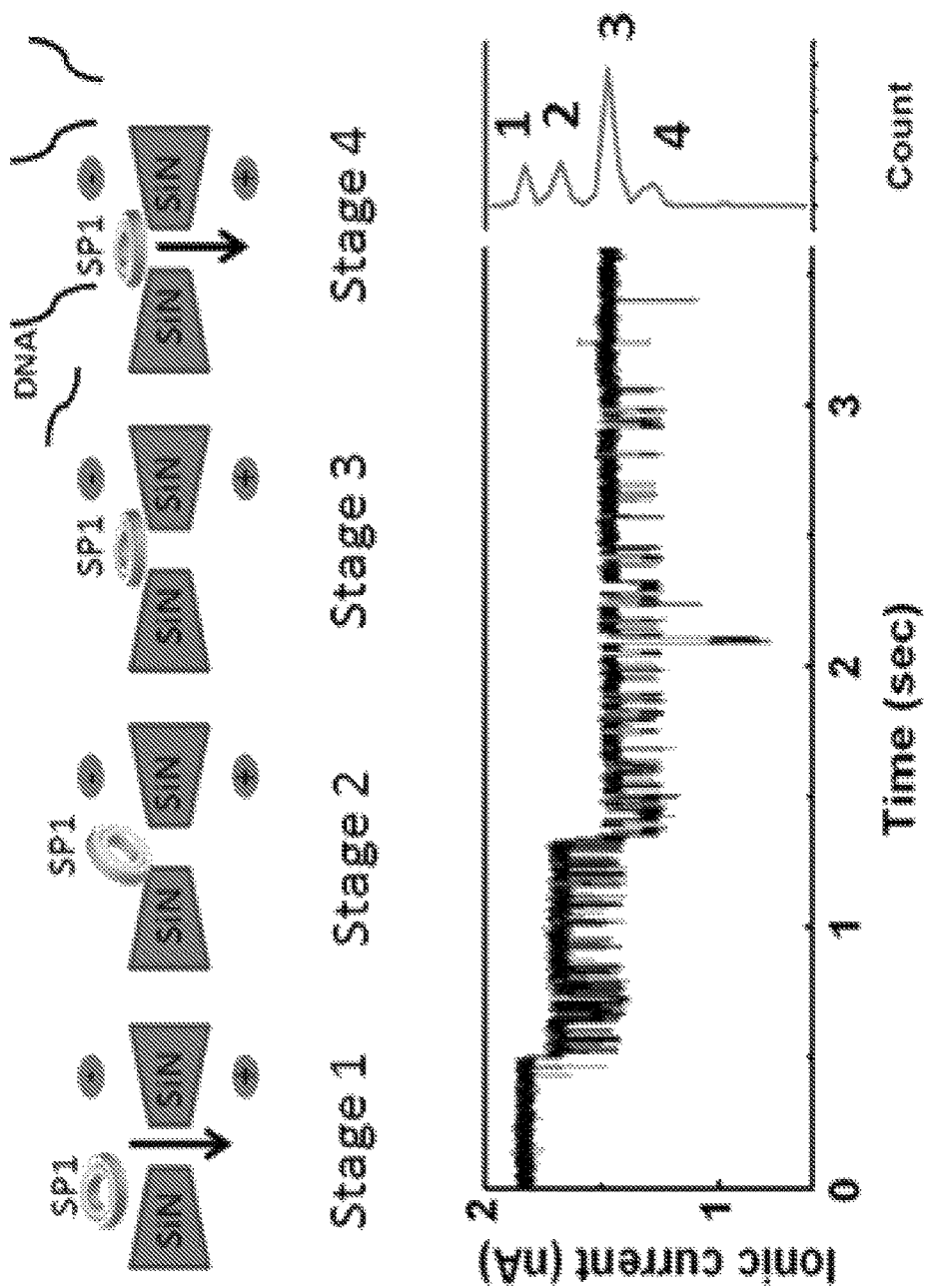
FIGS. 3A-3G show DNA translocation in SP1 hybrid nanopore.

The first three stages in the scheme shown in FIG. 3A were similar to the SP1 trapping described above. After mixing SP1 proteins and dsDNA molecules in the cis chamber, another set of blocking events was observed along the trapped SP1 level.

Figure 3B:
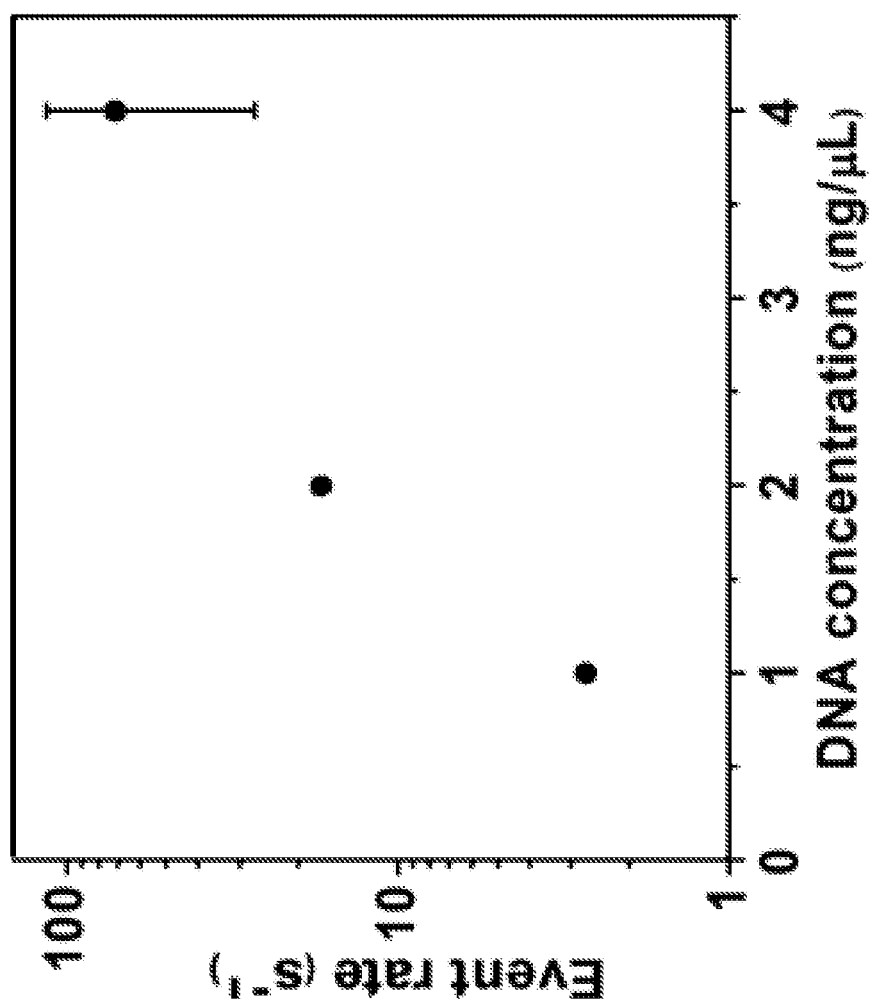

These additional events were attributed to DNA translocation through the hybrid SP1-SiN nanopore. In addition, their events frequency was increased as the DNA concentration was increased (FIG. 3B).

Figure 3C:
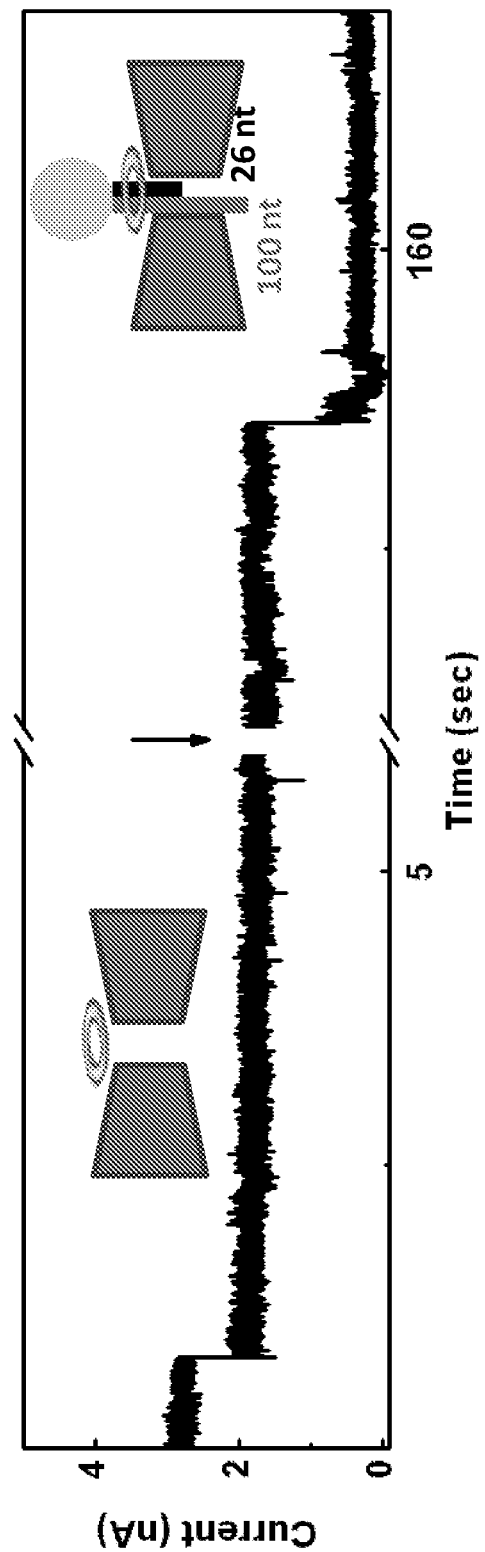

To further verify that the DNA was translocated through the nanopore, 10 nm gold nanoparticle conjugated to 26 bp single-stranded DNA hybridized to 100 bp single-stranded DNA was added to the solution and translocated into the hybrid nanopore, resulting in a much deeper (drop to 10-30% of the baseline) blockage of the SP1 pore by the nanoparticle (FIG. 3C).

Figure 3D:
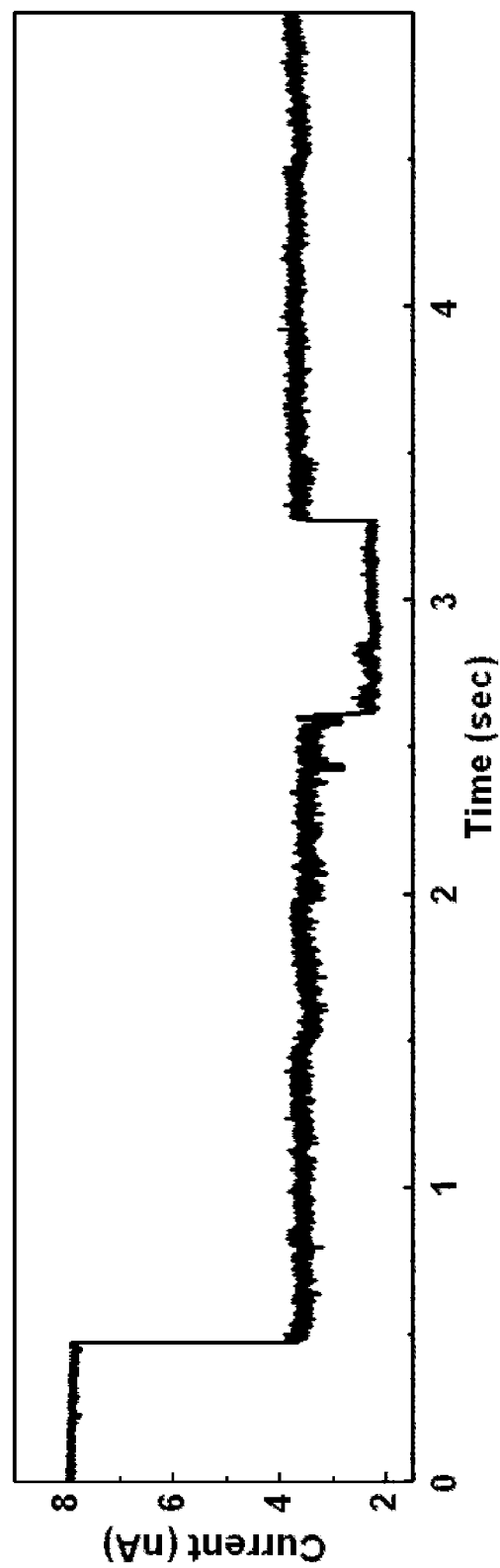

Such clogging could last for seconds unless the conjugated DNA is dehybridized or dissociated from the gold nanoparticle by the electrical force (FIG. 3D).

This further strengthens the suggestions that SP1 was sitting atop the SiN nanopore in a horizontal manner. These experiments confirm that dsDNA is indeed passing through the SP1-dressed nanopore and that the 4th peak in the histogram in FIG. 3A corresponds to dsDNA translocation.

Figure 3E:
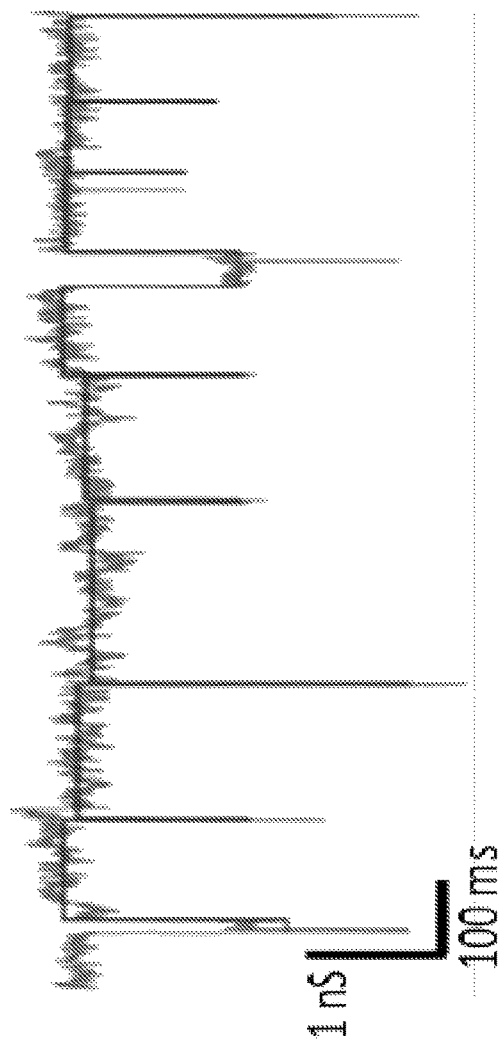
Figure 3F:
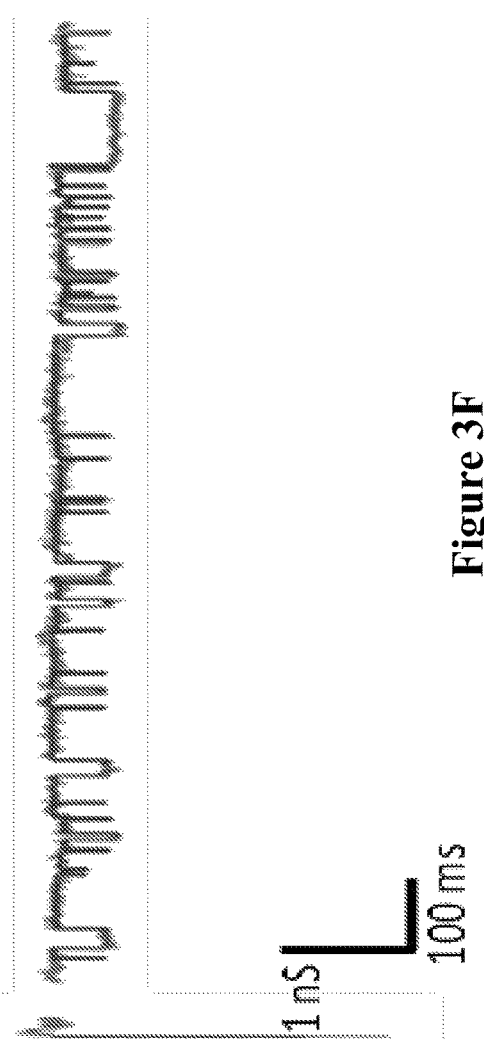

FIGS. 3E and 3F show a comparison between translocation of λ-DNA, 48 kbp, through a bare nanopore (FIG. 3E) and through the hybrid, SP1 dressed, nanopore (FIG. 3F). The uniform blocking level of the events in the hybrid, SP1 dressed, nanopore trace demonstrated that dsDNA which is translocated through the hybrid nanopore has a single conformation, likely linear, as opposed to DNA translocation through the bare solid state nanopore that shows multiple conformations.

Figure 3G:
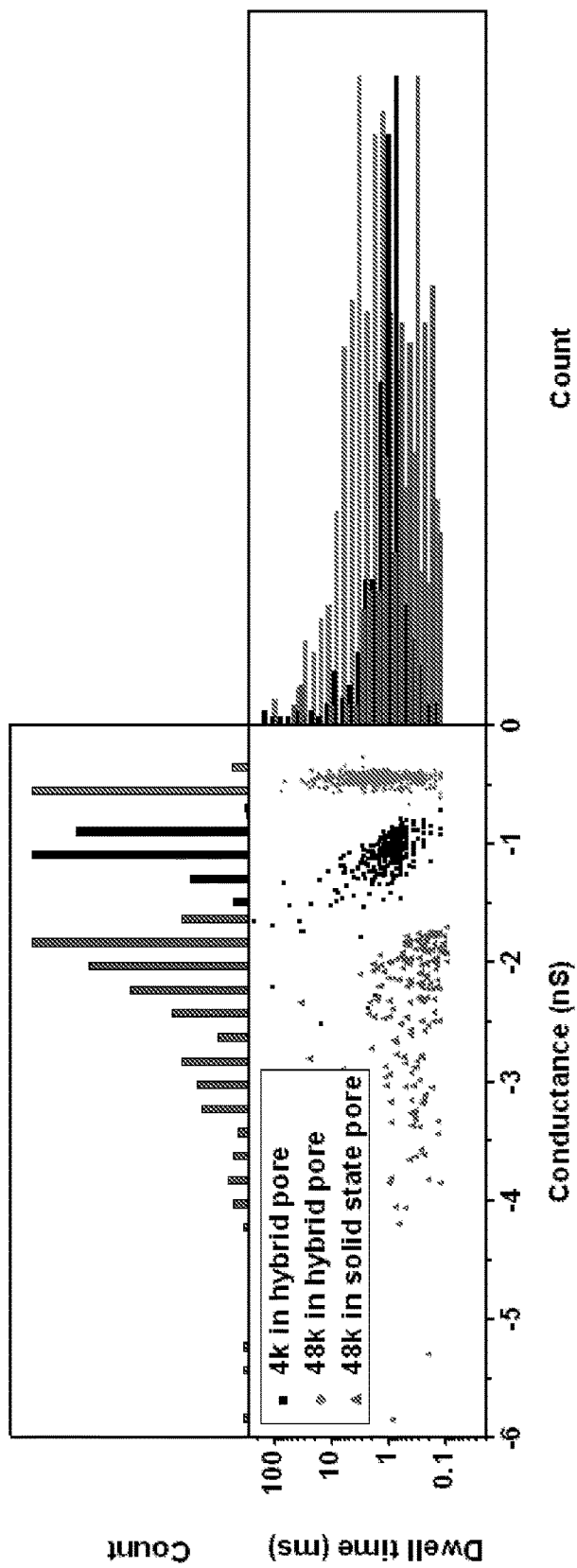

FIG. 3G provides a summary n comparison, using a scatter plot and histograms, of the conductance and dwell time of 48 kbp λ-DNA translocated through L81SP1 hybrid nanopore (dots) and through bare SiN nanopore (triangle).

The conductance histogram showed a single narrow peak for DNA translocation through the hybrid nanopore, suggesting a single linear DNA conformation with respect to multiple peaks for DNA translocation through the bare nanopore, suggesting variable DNA conformations.

dsDNA translocation through the hybrid nanopore blocks the ion current with a lower amplitude compared to dsDNA that is translocated through a bare nanopore (FIGS. 3E, 3F and 3G).

When the DNA is translocated through the bare nanopore in its linear form, it caused a reduction of ~2 ns in the ion conductance.

For the hybrid nanopore, the reduction in the blocking conductance to ~0.5 ns (FIGS. 3E, 3F and 3G) may be related to charge screening by the intrinsic positive charge in the inner pore of the SP 1.

Without being bound by theory, such a charge screening can lead to a reduced ion flow, resulting in lower blocking conductance.

In addition, the DNA translocation dwell time through the hybrid nanopore is longer by over an order of magnitude than the dwell time of translocation through the bare nanopore, as observed by monitoring the kinetics of the DNA translocation through the hybrid nanopore (FIG. 3G and FIG. 4).

Without being bound by theory, it was suggested that the slowing down in the dwell time through the hybrid nanopore may result from either the intrinsic positive charge residing in the inner pore of the SP1 or from a possible higher friction. These two parameters that can be controlled by using genetically or chemically modified SP1.

Since electrophoretic dragging of the DNA through the pore was the kinetic driving force, it was expected to obtain an exponential dependence of dwell time on the voltage.

Figure 4A:
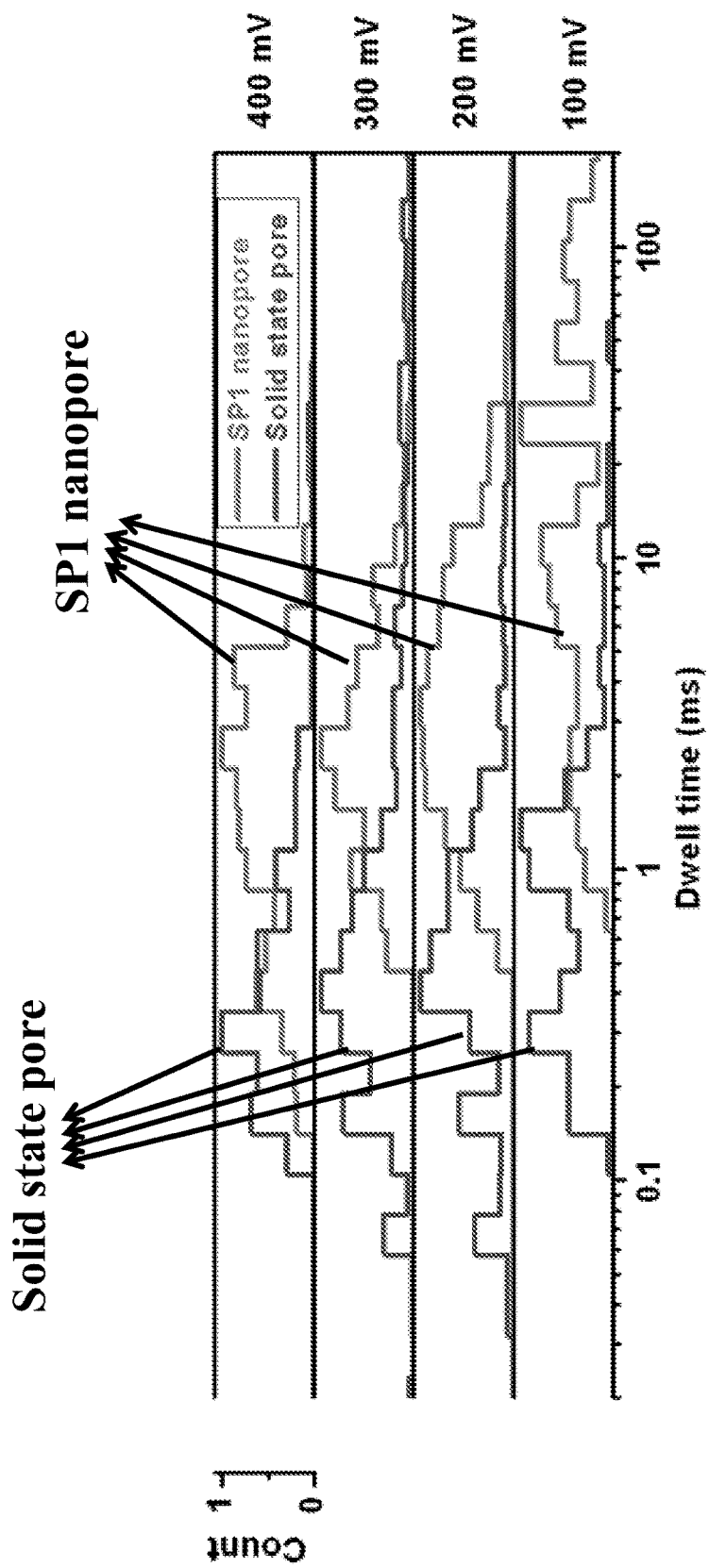
FIGS. 4A-4B are graphs showing that DNA translocation is slower through the SP1 hybrid nanopore.

FIG. 4A demonstrates the dwell time distribution of DNA translocation measured at various driving voltages from 100, 200 and 300 mV for the SiSP1 and at 400 mV for L81CSP1.

Figure 4B:
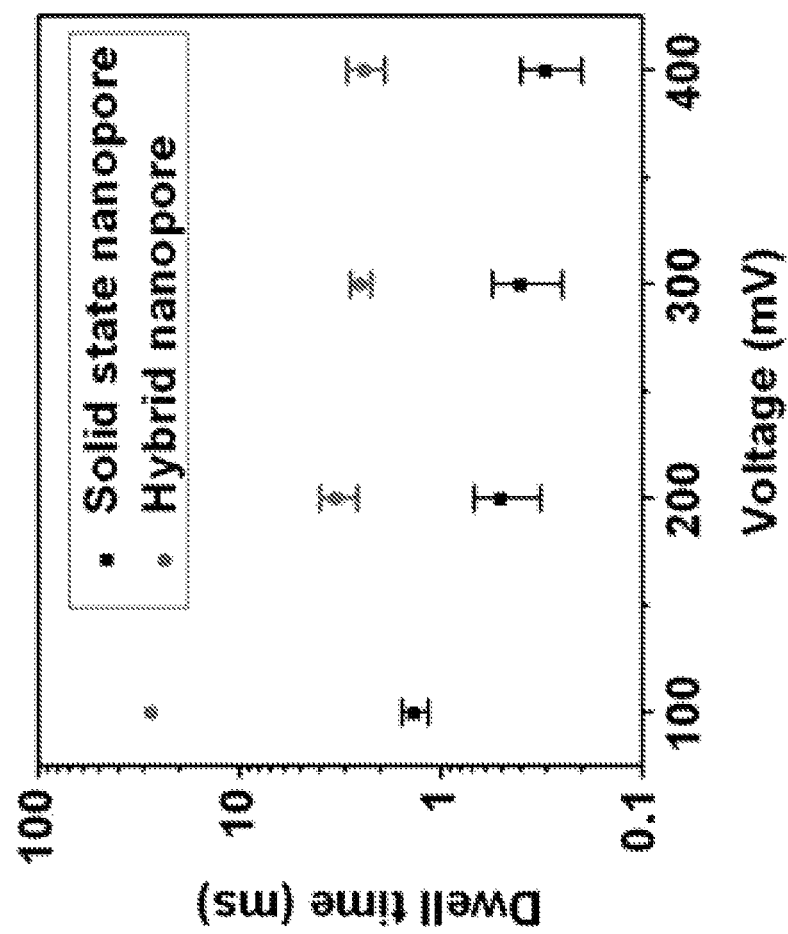

The peak of the distribution is the most probable dwell time for translocation and is plotted in FIG. 4B.

For both bare and hybrid nanopores, an exponential dependence of the dwell time on the voltage was observed, which is in agreement with electrophoretic-force driven translocation.

These results suggested that dsDNA is translocated through the trapped SP1. Compared to bare nanopores, the DNA translocation was slowed down by at least 10 fold for all the voltages (FIG. 4). This suggested that the absolute translocation velocity of dsDNA was dominated by the interaction between the protein and the DNA translocating through the pore.

The hybrid nanopore was shown to have at least three central advantages over the bare solid state nanopore.

First it enabled to slow down the translocation by over an order of magnitude. A further slow down might be achieved by genetic or chemical modification of the SP1 protein, thus addressing one of the central challenges on the track to DNA sequencing. An analysis that does not take into account very fast hitting attempts of the DNA on the SP1 as translocation events provides a further relative slowdown, up to nearly two orders of magnitude. The validity of such analysis must be, however, further controlled and verified.

Secondly, it allows translocation in a linear conformation only, unlike the bare solid state nanopore, where numerous conformations are observed that distort the translocation pattern shape and affect the translocation dwell time and naturally also the ability to sequence the translocated nucleotides.

The third advantage of the SP1 protein is its readiness for genetic engineering and functional modifications, in addition to its extreme stability.

The invention claimed is:

1. A hybrid structure comprising (a) a solid substrate having at least one nanopore perforating therethrough, and (b) at least one ring-like polypeptide situated at a region of said at least one nanopore, said region being selected from an opening of the nanopore and an interior region of said nanopore, wherein the binding of the at least one like polypeptide to the nanopore being different from covalent binding and wherein the at least one ring-like polypeptide is stable protein 1 (SP1).

2. The hybrid structure according to claim 1, wherein the at least one nanopore having an opening at a first surface of the substrate and a further opening at an opposite surface of the substrate, and interior surface spanning the opening at a first and the further opening at the opposite surface.

3. The hybrid structure according to claim 1, wherein the at least one ring-like polypeptide being situated at an opening of the nanopore at a first surface of the substrate.

4. The hybrid structure according to claim 1, wherein the SP1 polypeptide is a homo-dodecamer or hetero-dodecamer oligomeric polypeptide.

5. The hybrid structure according to claim 1, wherein at least one of the SP1 polypeptide monomers is wild type SP1 polypeptide having an amino acid sequence denoted by SEQ ID NO:1.

6. The hybrid structure according to claim 5, wherein at least one of the SP1 polypeptide monomers is encoded by the polynucleotide deposited in NCBI under GenBank: AJ276517.1 (SEQ ID NO:8).

7. The hybrid structure according to claims 1, wherein at least one of the SP1 polypeptide monomers having an amino acid sequence denoted by any one of SEQ ID NO:2, SEQ ID NO:3, SEQ ID NO:4, SEQ ID NO:5, SEQ ID NO:6, SEQ ID NO:7, SEQ ID NO:15 and SEQ ID NO:17.

8. A self assembled hybrid structure comprising (a) a solid substrate having at least one nanopore perforating therethrough, and (b) at least one ring-like polypeptide situated at a region of said at least one nanopore, said region being selected from an opening of the nanopore and an interior region of said nanopore, wherein the at least one ring-like polypeptide is stable protein 1 (SP1).

9. A device comprising:
(i) a hybrid structure comprising (a) a solid substrate having at least one nanopore perforating therethrough, and (b) at least one ring-like polypeptide situated at a region of said at least one nanopore, said region being selected from an opening of the nanopore and an interior region of said nanopore, wherein the binding of the at least one ring-like polypeptide to the nanopore being different from covalent binding, and wherein the at least one ring-like polypeptide is stable protein 1 (SP1); and
(ii) a measuring unit.

10. The device according to claim 9, wherein the at least one nanopore having an opening at a first surface of the substrate and a further opening at an opposite surface of the substrate, and interior surface spanning the opening at a first surface and the further opening at the opposite surface.

11. The device according to claim 9, comprising an electrode assembly.

12. The device according to claim 9, comprising a voltage source.

* * * * *